(12) United States Patent
Jackson

(10) Patent No.: US 8,814,911 B2
(45) Date of Patent: Aug. 26, 2014

(54) POLYAXIAL BONE SCREW WITH CAM CONNECTION AND LOCK AND RELEASE INSERT

(76) Inventor: Roger P. Jackson, Prairie Village, KS (US)

( * ) Notice: Subject to any disclaimer, the term of this patent is extended or adjusted under 35 U.S.C. 154(b) by 492 days.

(21) Appl. No.: 13/068,504

(22) Filed: May 12, 2011

(65) Prior Publication Data

US 2011/0218578 A1 Sep. 8, 2011

Related U.S. Application Data

(63) Continuation-in-part of application No. 12/009,130, filed on Jan. 16, 2008, now Pat. No. 8,257,398, which is a continuation-in-part of application No. 10/818,554, filed on Apr. 5, 2004, now Pat. No. 7,662,175, which is a continuation of application No. 10/464,633, filed on Jun. 18, 2003, now Pat. No. 6,716,214, which is a continuation-in-part of application No. 10/651,003, filed on Aug. 28, 2003, now Pat. No. 8,137,386, application No. 13/068,504, which is a continuation-in-part of application No. 12/154,460, filed on May 23, 2008, now Pat. No. 8,257,396, which is a continuation-in-part of application No. 11/140,343, filed on May 27, 2005, now Pat. No. 7,776,067, which is a continuation-in-part of application No. 12/804,580, filed on Jul. 23, 2010, now Pat. No. 8,394,133, which is a continuation of application No. 11/522,503, filed on Sep. 14, 2006, now Pat. No. 7,766,915, which is a continuation-in-part of application No. 11/024,543, filed on Dec. 20, 2004, now Pat. No. 7,204,838.

(60) Provisional application No. 61/395,692, filed on May 14, 2010, provisional application No. 60/881,641, filed on Jan. 22, 2007, provisional application No. 60/931,362, filed on May 23, 2007.

(51) Int. Cl.
A61B 17/70 (2006.01)
A61B 17/86 (2006.01)

(52) U.S. Cl.
CPC ................................ *A61B 17/86* (2013.01)
USPC .............................................. 606/264

(58) Field of Classification Search
USPC .......... 606/246, 250, 251, 257, 264–272, 301, 606/305, 308
See application file for complete search history.

(56) References Cited

U.S. PATENT DOCUMENTS

| 2,346,346 A | 4/1944 | Anderson |
|---|---|---|
| 2,362,999 A | 11/1944 | Elmer |

(Continued)

FOREIGN PATENT DOCUMENTS

| DE | 9202745.8 | 4/1992 |
|---|---|---|
| DE | 19507141 | 9/1996 |

(Continued)

OTHER PUBLICATIONS

*EBI Omega 21* Brochure, EBI Spine Systems, pub. 1999.

(Continued)

*Primary Examiner* — Pedro Philogene
*Assistant Examiner* — David Comstock
(74) *Attorney, Agent, or Firm* — John C. McMahon

(57) ABSTRACT

A polyaxial bone screw assembly includes a threaded shank body having an integral upper portion receivable in a receiver, the receiver having an upper channel for receiving a longitudinal connecting member and a lower cavity cooperating with a lower opening. A retaining member for capturing the shank in the receiver includes a sloping surface for a frictional, press fit, cammed engagement with the shank. A compression insert having a resilient structure provides non-floppy positioning of the shank with respect to the receiver and also independent locking of the shank with respect to the receiver.

38 Claims, 22 Drawing Sheets

(56) References Cited

U.S. PATENT DOCUMENTS

| | | |
|---|---|---|
| 2,531,892 A | 11/1950 | Reese |
| 2,813,450 A | 11/1957 | Dzus |
| 3,013,244 A | 12/1961 | Rudy |
| 4,033,139 A | 7/1977 | Frederick |
| 4,759,672 A | 7/1988 | Nilsen et al. |
| 4,790,297 A | 12/1988 | Luque |
| 4,946,458 A | 8/1990 | Harms et al. |
| 5,019,080 A | 5/1991 | Hemer |
| 5,129,388 A | 7/1992 | Vignaud et al. |
| 5,207,678 A | 5/1993 | Harms et al. |
| 5,261,912 A | 11/1993 | Frigg |
| 5,312,404 A | 5/1994 | Asher et al. |
| 5,360,431 A | 11/1994 | Puno et al. |
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,647,873 A | 7/1997 | Errico et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,392 A | 11/1997 | Richelsoph |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,938,663 A | 8/1999 | Petreto |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,547,790 B2 | 4/2003 | Harkey, III et al. |
| 6,551,320 B2 | 4/2003 | Lieberman |
| 6,554,832 B2 | 4/2003 | Shluzas |
| 6,554,834 B2 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |

(56) References Cited

U.S. PATENT DOCUMENTS

| | | |
|---|---|---|
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,677 B1 | 5/2005 | Lin |
| 6,932,817 B2 | 8/2005 | Baynham et al. |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,426 B2 | 10/2006 | Moumene et al. |
| 7,128,743 B2 | 10/2006 | Metz-Stavenhagen |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,211,086 B2 | 5/2007 | Biedermann |
| 7,211,087 B2 | 5/2007 | Young |
| 7,214,227 B2 | 5/2007 | Colleran et al. |
| 7,223,268 B2 | 5/2007 | Biedermann |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mjuwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,641,674 B2 | 1/2010 | Young |
| 7,645,294 B2 | 1/2010 | Kalfas et al. |
| 7,648,522 B2 | 1/2010 | David |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,497 B2 | 4/2010 | Cordaro et al. |
| 7,695,498 B2 | 4/2010 | Ritland |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,258 B2 | 7/2010 | Biedermann et al. |
| 7,758,618 B2 | 7/2010 | Walder et al. |
| 7,763,057 B2 | 7/2010 | Abdelgany et al. |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,819,902 B2 | 10/2010 | Abdelgany et al. |
| 2001/0001119 A1 | 5/2001 | Lombardo |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |

(56) References Cited

U.S. PATENT DOCUMENTS

| | | |
|---|---|---|
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096654 A1 | 5/2005 | Lin |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0260058 A1 | 11/2005 | Casagne, III |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079899 A1 | 4/2006 | Ritland |
| 2006/0084981 A1 | 4/2006 | Shluzas |
| 2006/0084989 A1 | 4/2006 | Dickinson et al. |
| 2006/0084993 A1 | 4/2006 | Landry et al. |
| 2006/0084995 A1 | 4/2006 | Biedermann et al. |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106383 A1 | 5/2006 | Biedermann et al. |
| 2006/0116677 A1 | 6/2006 | Burd et al. |
| 2006/0129147 A1 | 6/2006 | Biedermann et al. |
| 2006/0129149 A1 | 6/2006 | Iott et al. |
| 2006/0142761 A1 | 6/2006 | Landry et al. |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfiled et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0195098 A1 | 8/2006 | Schumacher |
| 2006/0200123 A1 | 9/2006 | Ryan |
| 2006/0200131 A1 | 9/2006 | Chao et al. |
| 2006/0200149 A1 | 9/2006 | Hoy et al. |
| 2006/0212034 A1 | 9/2006 | Triplett et al. |
| 2006/0217716 A1 | 9/2006 | Baker et al. |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0247624 A1 | 11/2006 | Banouskou et al. |
| 2006/0247631 A1 | 11/2006 | Ahn et al. |
| 2006/0247636 A1 | 11/2006 | Yuan et al. |
| 2006/0247779 A1 | 11/2006 | Gordon et al. |
| 2006/0264933 A1 | 11/2006 | Baker et al. |
| 2006/0264936 A1 | 11/2006 | Partin et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0293659 A1 | 12/2006 | Alvarez |
| 2006/0293665 A1 | 12/2006 | Shluzas |
| 2006/0293666 A1 | 12/2006 | Matthis et al. |
| 2007/0016188 A1 | 1/2007 | Boehm, Jr. et al. |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |

(56) References Cited

U.S. PATENT DOCUMENTS

| | | |
|---|---|---|
| 2007/0049933 A1 | 3/2007 | Ahn et al. |
| 2007/0055235 A1 | 3/2007 | Janowski et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0073291 A1 | 3/2007 | Cordaro et al. |
| 2007/0078460 A1 | 4/2007 | Frigg et al. |
| 2007/0083199 A1 | 4/2007 | Baccelli |
| 2007/0088357 A1 | 4/2007 | Johnson et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123867 A1 | 5/2007 | Kirschman |
| 2007/0123870 A1 | 5/2007 | Jeon et al. |
| 2007/0161986 A1 | 7/2007 | Levy |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173819 A1 | 7/2007 | Sandlin |
| 2007/0173820 A1 | 7/2007 | Trieu |
| 2007/0173828 A1 | 7/2007 | Firkins et al. |
| 2007/0191839 A1 | 8/2007 | Justis et al. |
| 2007/0198014 A1 | 8/2007 | Graf et al. |
| 2007/0208344 A1 | 9/2007 | Young |
| 2007/0225707 A1 | 9/2007 | Wisnewski et al. |
| 2007/0225711 A1 | 9/2007 | Ensign |
| 2007/0233078 A1 | 10/2007 | Justis et al. |
| 2007/0233080 A1 | 10/2007 | Na et al. |
| 2007/0233086 A1 | 10/2007 | Harms et al. |
| 2007/0233087 A1 | 10/2007 | Schlapfer |
| 2007/0250061 A1 | 10/2007 | Chin et al. |
| 2007/0260243 A1 | 11/2007 | Kagami |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270815 A1 | 11/2007 | Johnson et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270839 A1 | 11/2007 | Jeon et al. |
| 2007/0288004 A1 | 12/2007 | Alvarez |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021473 A1 | 1/2008 | Butler et al. |
| 2008/0027432 A1 | 1/2008 | Strauss et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0058811 A1 | 3/2008 | Alleyne et al. |
| 2008/0058812 A1 | 3/2008 | Zehnder |
| 2008/0065073 A1 | 3/2008 | Perriello et al. |
| 2008/0065075 A1 | 3/2008 | Dant |
| 2008/0065077 A1 | 3/2008 | Ferree |
| 2008/0071273 A1 | 3/2008 | Hawkes et al. |
| 2008/0071274 A1 | 3/2008 | Enisgn |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0140075 A1 | 6/2008 | Ensign et al. |
| 2008/0154315 A1 | 6/2008 | Jackson |
| 2008/0161859 A1 | 7/2008 | Nilsson |
| 2008/0161863 A1 | 7/2008 | Arnold et al. |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0195159 A1 | 8/2008 | Kloss et al. |
| 2008/0200956 A1 | 8/2008 | Beckwith et al. |
| 2008/0215095 A1 | 9/2008 | Biedermann et al. |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0249570 A1 | 10/2008 | Carson et al. |
| 2008/0249576 A1 | 10/2008 | Wawkes et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1 | 10/2008 | Garamszegi |
| 2008/0287994 A1 | 11/2008 | Perez-Cruet et al. |
| 2008/0288002 A1 | 11/2008 | Crall et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Battlers et al. |
| 2008/0312701 A1 | 12/2008 | Batters et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |

(56) References Cited

U.S. PATENT DOCUMENTS

| | | |
|---|---|---|
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0057125 A1 | 3/2010 | Viker |
| 2010/0057126 A1 | 3/2010 | Hestad |
| 2010/0063545 A1 | 3/2010 | Richelsoph |
| 2010/0063546 A1 | 3/2010 | Miller et al. |
| 2010/0063550 A1 | 3/2010 | Felix et al. |
| 2010/0063551 A1 | 3/2010 | Richelsoph |
| 2010/0063553 A1 | 3/2010 | Warnick |
| 2010/0069963 A1 | 3/2010 | Eckman |
| 2010/0069969 A1 | 3/2010 | Ampuero et al. |
| 2010/0087861 A1 | 4/2010 | Lechmann et al. |
| 2010/0087865 A1 | 4/2010 | Biedermann et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0114170 A1 | 5/2010 | Barrus et al. |
| 2010/0114171 A1 | 5/2010 | Boachie-Adjei et al. |
| 2010/0114180 A1 | 5/2010 | Rock et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0152788 A1 | 6/2010 | Warnick |
| 2010/0160965 A1 | 6/2010 | Viker |
| 2010/0160974 A1 | 6/2010 | Viker |
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0174322 A1 | 7/2010 | Abdelgany et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222822 A1 | 9/2010 | Farris et al. |
| 2010/0228293 A1 | 9/2010 | Courtney et al. |
| 2010/0234891 A1 | 9/2010 | Freeman et al. |
| 2010/0241170 A1 | 9/2010 | Cammisa et al. |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0262196 A1 | 10/2010 | Barrus et al. |

FOREIGN PATENT DOCUMENTS

| | | |
|---|---|---|
| EP | 1121902 | 8/2001 |
| EP | 1190678 | 3/2002 |
| EP | 1210914 | 6/2002 |
| EP | 1570795 | 9/2005 |
| EP | 1579816 | 9/2005 |
| EP | 1634537 | 3/2006 |
| EP | 1925263 | 5/2008 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 2365345 | 2/2002 |
| WO | WO95/01132 | 1/1995 |
| WO | WO01/10317 | 2/2001 |
| WO | WO02/054966 | 7/2002 |
| WO | WO03/068088 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |

OTHER PUBLICATIONS

*Claris Instrumentation* Brochure, G Med, pub. 1997.
*VLS System Variable Locking Screw* Brochure, Interpore Cross International, 1999.
*CD Horizon M8 Multi Axial Screw Spinal System* Brochure, Medtronic Sofamor Danek, no publish date.
*Contour Spinal System* Brochure, Ortho Development, no publish date.
*Xia Spinal System* Brochure, Stryker Howmedica Osteonics, no publish date.

(56) References Cited

OTHER PUBLICATIONS

*The Rod Plate System* Brochure, Stryker Howmedica Osteonics, pub. Oct. 1999.
*Silhouette Spinal Fixation System* Brochure, Sulzer Medica Spine-Tech, no publish date.
*SDSR Surgical Dynamics Rod System* Brochure, Surgical Dynamics, pub. 1998-99.
*Versalok Low Back Fixation System* Brochure, Wright Medical Technology, Inc., pub. 1997.
*The Strength of Innovation Advertisement*, Blackstone Medical Inc., no publish date.
*The Moss Miami 6.0mm System* Advertisement, author unknown, no publish date.

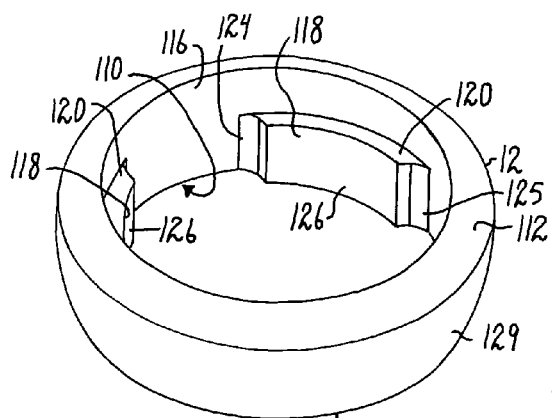
Fig.14.
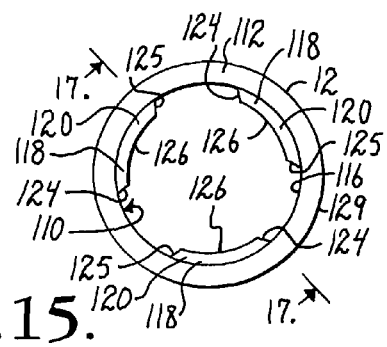
Fig.15.
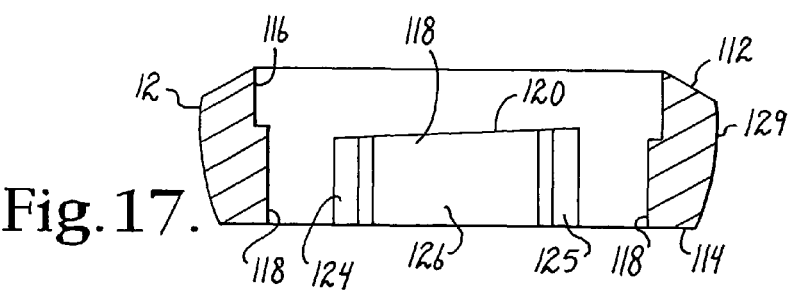
Fig.17.
Fig.18.
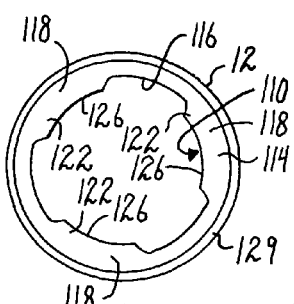
Fig.16.
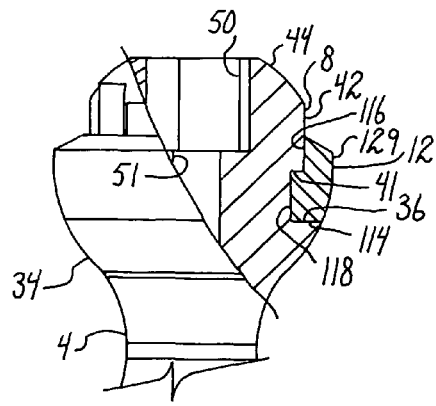

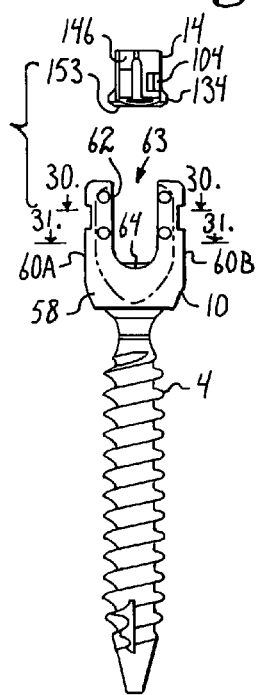
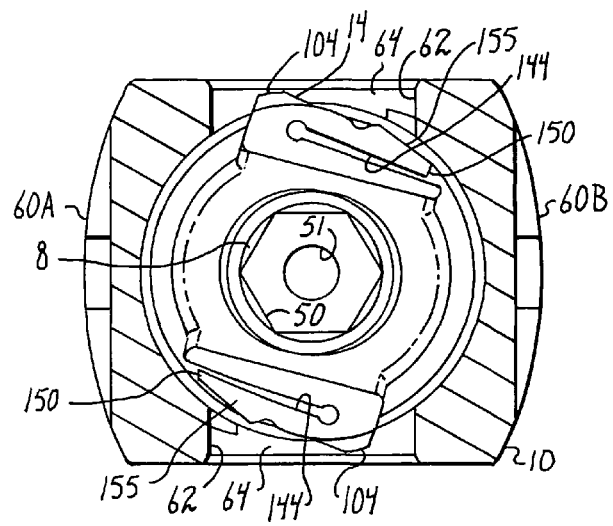
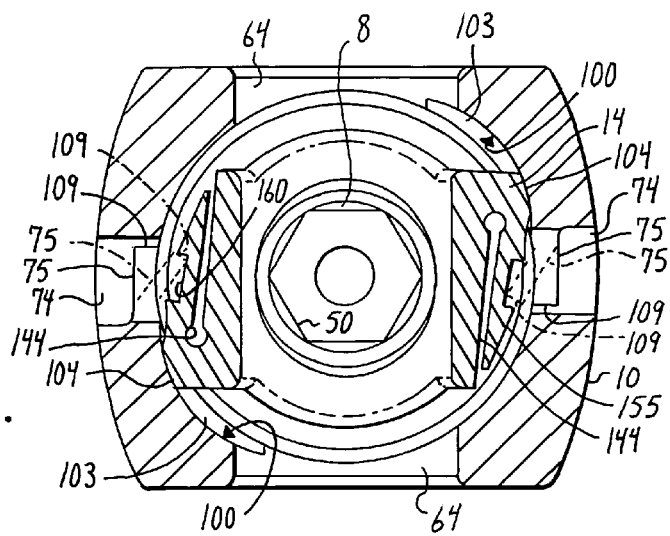
Fig.29.
Fig.30.
Fig.31.

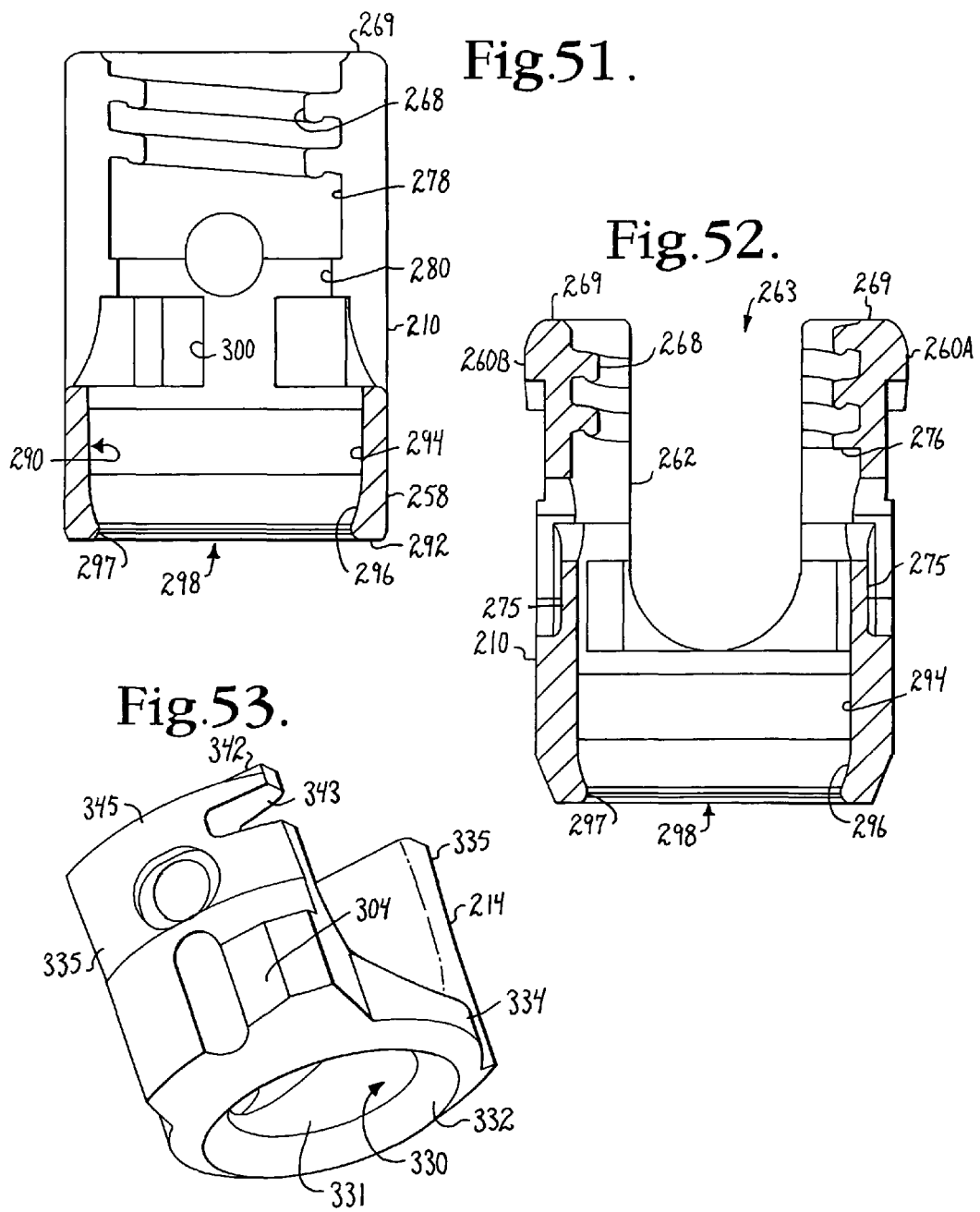

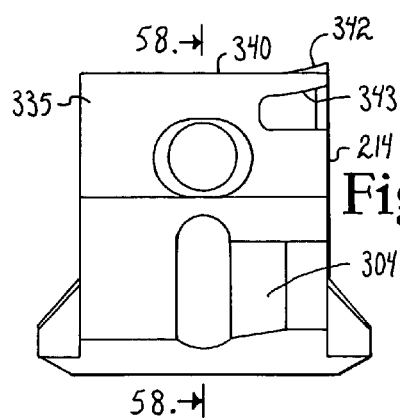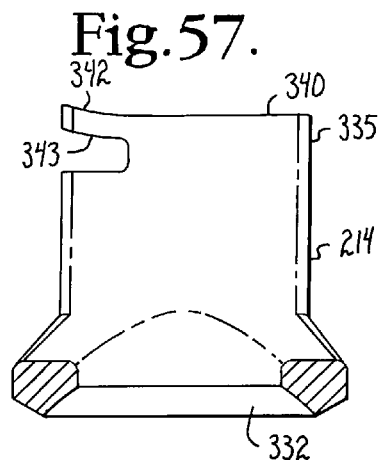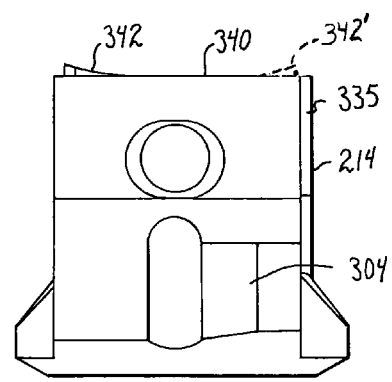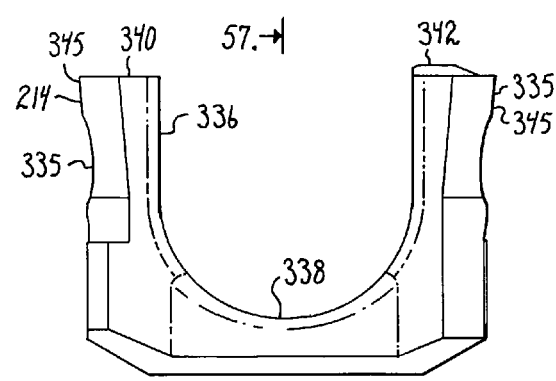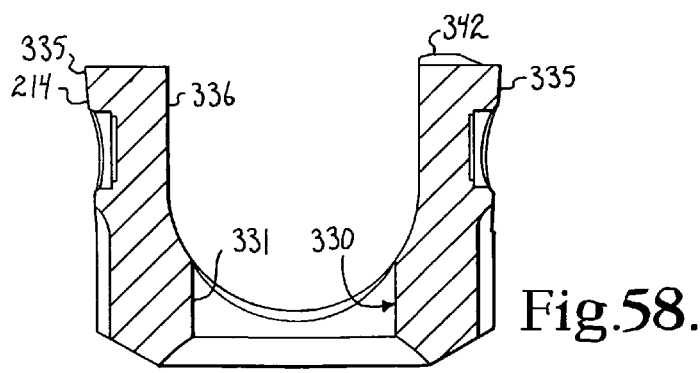

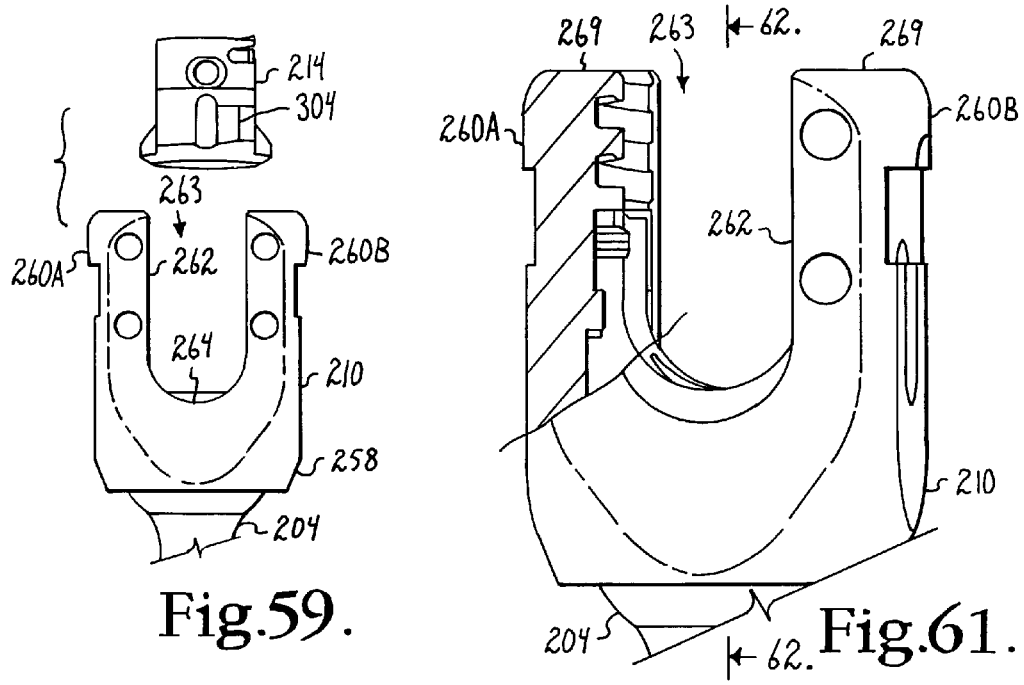
Fig.59.
Fig.61.
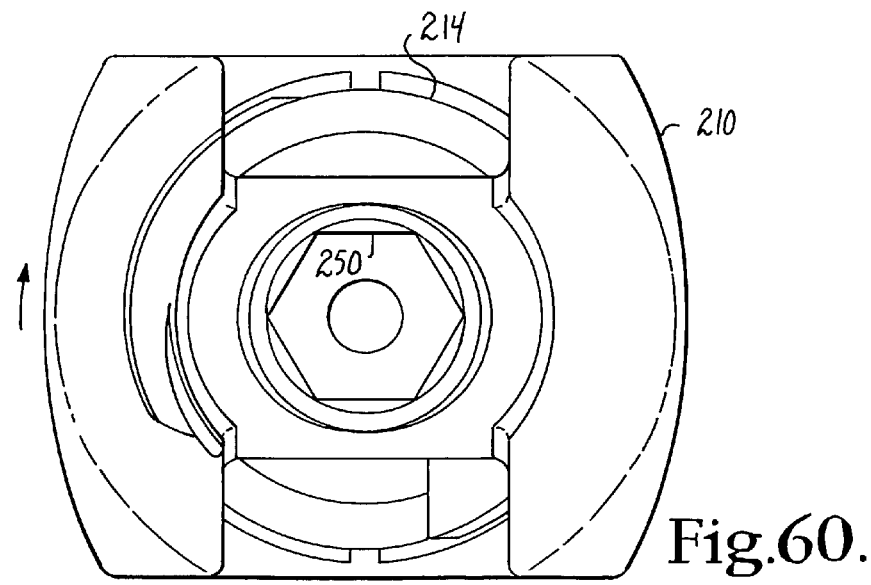
Fig.60.

POLYAXIAL BONE SCREW WITH CAM CONNECTION AND LOCK AND RELEASE INSERT

CROSS-REFERENCE TO RELATED APPLICATIONS

This application claims the benefit of U.S. Prov. Pat. App. Ser. No. 61/395,692, filed May 14, 2010 and incorporated by reference herein. This application is also a continuation-in-part of U.S. patent application Ser. No. 12/009,130 filed Jan. 16, 2008 that claims the benefit of U.S. Prov. Pat. App. Ser. No. 60/881,641 filed Jan. 22, 2007 and is a continuation-in-part of U.S. patent application Ser. No. 10/818,554, filed Apr. 5, 2004, now U.S. Pat. No. 7,662,175, which is a continuation of U.S. patent application Ser. No. 10/464,633, filed Jun. 18, 2003, now U.S. Pat. No. 6,716,214; and also U.S. patent application Ser. No. 10/818,554 being a continuation-in-part of U.S. patent application Ser. No. 10/651,003, filed Aug. 28, 2003, all of the disclosures of which are incorporated by reference herein. This application is also a continuation-in-part of U.S. patent application Ser. No. 12/154,460 filed May 23, 2008 that claims the benefit of U.S. Prov. Pat. App. Ser. No. 60/931,362 filed May 23, 2007 and is a continuation-in-part of U.S. patent application Ser. No. 11/140,343 filed May 27, 2005, all of the disclosures of which are incorporated by reference herein. This application is a continuation-in-part of U.S. patent application Ser. No. 12/804,580 filed Jul. 23, 2010 that is a continuation of U.S. patent application Ser. No. 11/522,503 filed Sep. 14, 2006, now U.S. Pat. No. 7,766,915, that is a continuation-in-part of U.S. patent application Ser. No. 11/024,543 filed Dec. 20, 2004, now U.S. Pat. No. 7,204,838, all of the disclosures of which are incorporated by reference herein.

BACKGROUND OF THE INVENTION

The present invention is directed to polyaxial bone screws for use in bone surgery, particularly spinal surgery and particularly to such screws with compression or pressure inserts.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke with a U-shaped slot or channel to receive, a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as a rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred.

Open-ended polyaxial bone screws allow rotation of the head or receiver about the shank until a desired rotational position of the head is achieved relative to the shank. Thereafter, a rod or other longitudinal connecting member can be inserted into the head or receiver and eventually the receiver is locked or fixed in a particular position relative to the shank. During the rod implantation process it is desirable to utilize bone screws or other bone anchors that have components that remain within the bone screw and further remain properly aligned during what is sometimes a very lengthy, difficult procedure.

SUMMARY OF THE INVENTION

A bone anchor assembly according to the invention includes a shank having an upper portion or head and a body for fixation to a bone; a receiver defining an upper open channel, a cavity and a lower opening; a compression insert; and a retainer for capturing the shank upper portion in the receiver, the retainer being in press fit engagement with the shank upper portion, the upper portion and attached retainer being pivotable with respect to the receiver prior to locking of the shank into a desired configuration. The press-fit engagement between the shank upper portion and the retainer may also be described as a cam capture, with the retainer and/or shank upper portion having a sloping or inclined surface. The shank and retainer cooperate in such a manner that a partial rotation between the retainer and the shank brings the shank and retainer structures into locking engagement. The illustrated compression insert operatively engages the shank upper portion and is spaced from the retainer. The compression insert frictionally engages the shank during assembly, providing non-floppy positioning of the shank with respect to the receiver and also subsequent independent locking of the shank with respect to the receiver. The non-floppy temporary frictional holding is provided by at least one resilient surface on the insert, compression of the resilient surface toward the insert during the temporary frictional holding is by an inner surface of the receiver. When the insert is pressed downwardly into locking engagement with the shank upper portion or head, the resilient surface returns to a neutral or near neutral position, resiliently pressing out against the receiver and locking the insert against the receiver. Thereafter, further manipulation of a rod or other longitudinal connecting member is possible with the otherwise locked screw.

Objects of the invention include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 14 is an enlarged perspective view of the retainer of FIG. 1.

FIG. 15 is an enlarged top plan view of the retainer of FIG. 1.

FIG. 16 is an enlarged bottom plan view of the retainer of FIG. 1.

FIG. 17 is an enlarged cross-sectional view taken along the line 17-17 of FIG. 15.

FIG. 18 is an enlarged and partial front elevational view of the shank and retainer of FIG. 1 with portions broken away to show the detail thereof.

FIG. 29 is a reduced front elevational view of the assembled receiver, retainer and shank of FIG. 28, showing a stage of assembly with the insert of FIG. 1, shown in a side elevational loading position.

FIG. 30 is an enlarged cross-sectional view of the receiver, retainer and shank taken along the line 30-30 of FIG. 29 and further showing the insert of FIG. 29 in top plan view, being shown in a stage of assembly within the receiver.

FIG. 31 is an enlarged cross-sectional view of the receiver, retainer and shank taken along the line 31-31 of FIG. 29 and further showing the insert of FIG. 29 in cross-section in a first factory assembled position within the receiver, and also showing in phantom the pair of receiver spring tabs being biased toward the insert.

FIG. 51 is an enlarged cross-sectional view taken along the line 51-51 of FIG. 50.

FIG. 52 is an enlarged cross-sectional view taken along the line 52-52 of FIG. 49.

FIG. 53 is an enlarged perspective view of the insert of FIG. 47.

FIG. 54 is an enlarged side elevational view of the insert of FIG. 47.

FIG. 55 is an enlarged side elevational view of the insert of FIG. 47 opposite to that shown in FIG. 54.

FIG. 56 is an enlarged front elevational view of the insert of FIG. 47.

FIG. 57 is a cross-sectional view taken along the line 57-57 of FIG. 56.

FIG. 58 is a cross-sectional view taken along the line 58-58 of FIG. 54.

FIG. 59 is an enlarged and partial front elevational view of the assembled receiver, retainer and shank of FIG. 47, shown in exploded view with the insert of FIG. 47, the insert being in a side elevational loading position.

FIG. 60 is an enlarged top plan view of the assembled receiver, retainer and shank of FIG. 47, further showing the insert of FIG. 47 in top plan view, being shown in a stage of assembly within the receiver.

FIG. 61 is an enlarged and partial perspective view of the assembled receiver, retainer, shank and insert of FIG. 47 with a portion of the receiver broken away to show the detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

Figure 1:
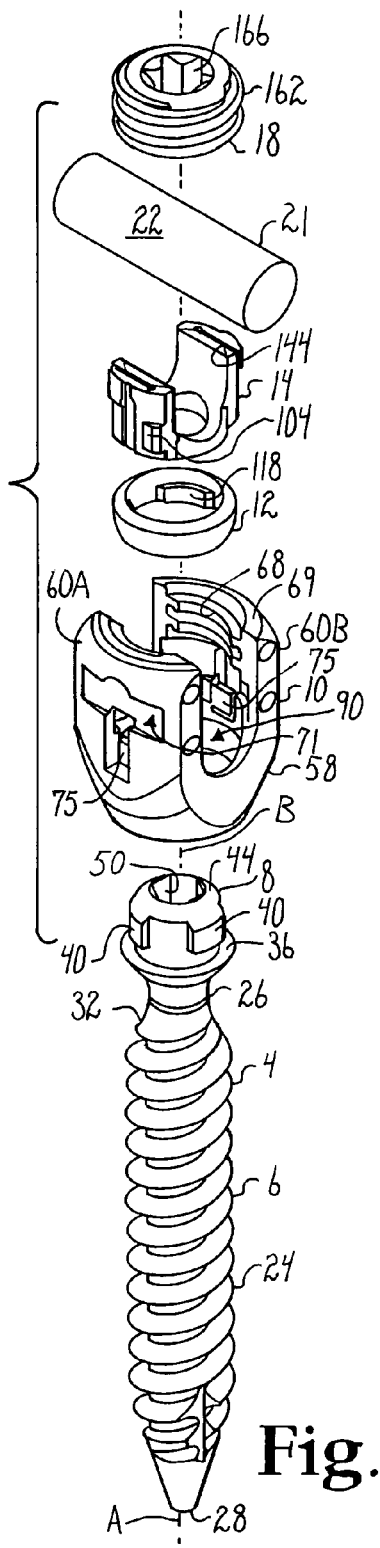
FIG. 1 is an exploded perspective view of a polyaxial bone screw assembly according to the present invention including a shank, a receiver, a retainer and a compression insert and also shown with a closure top and a longitudinal connecting member in the form of a rod.
Figure 2:
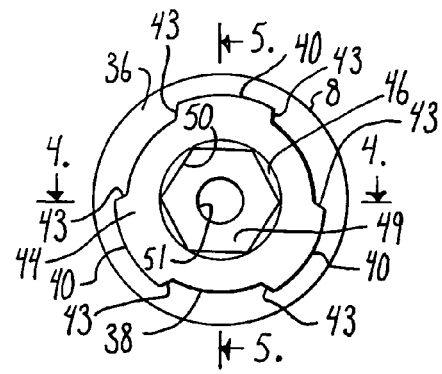
FIG. 2 is an enlarged top plan view of the shank of FIG. 1.
Figure 3:
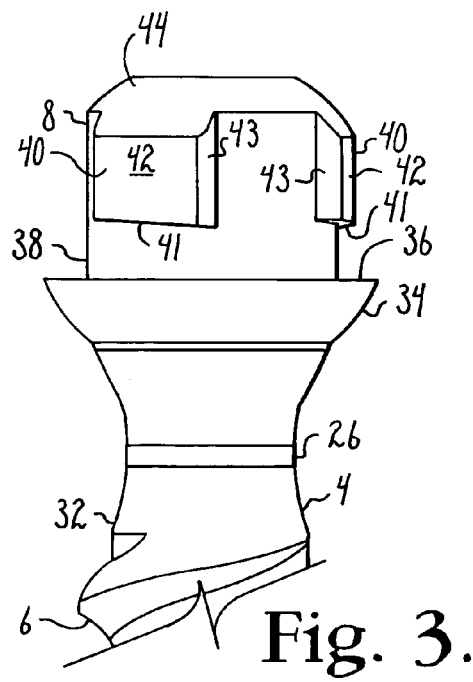
FIG. 3 is an enlarged and partial front elevational view of the shank of FIG. 1.
Figure 4:
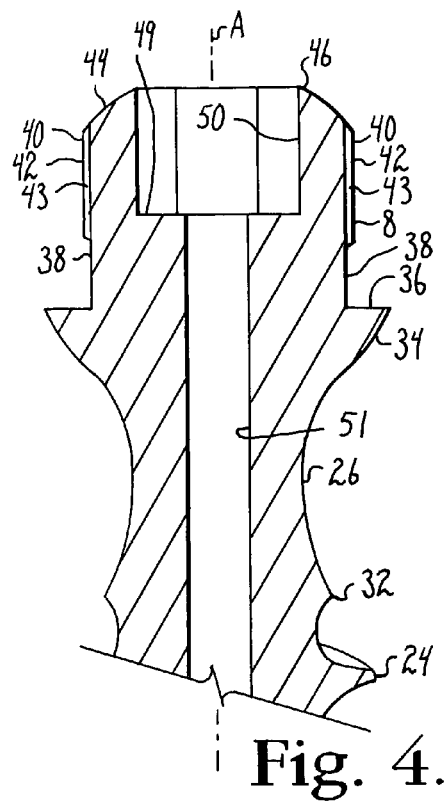
FIG. 4 is an enlarged and partial cross-sectional view taken along the line 4-4 of FIG. 2.
Figure 5:
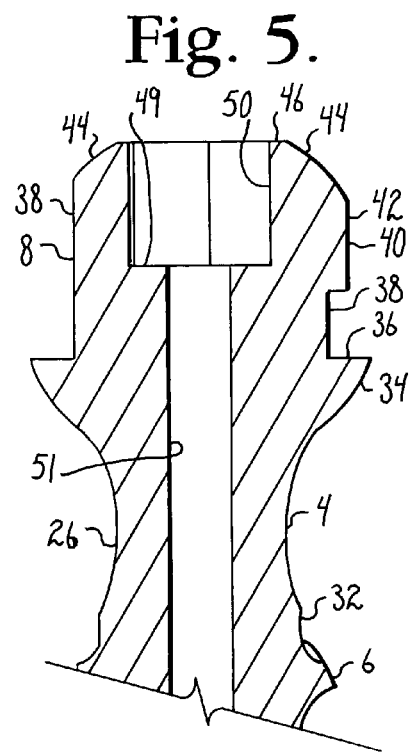
FIG. 5 is an enlarged and partial cross-sectional view taken along the line 5-5 of FIG. 2.
Figure 6:
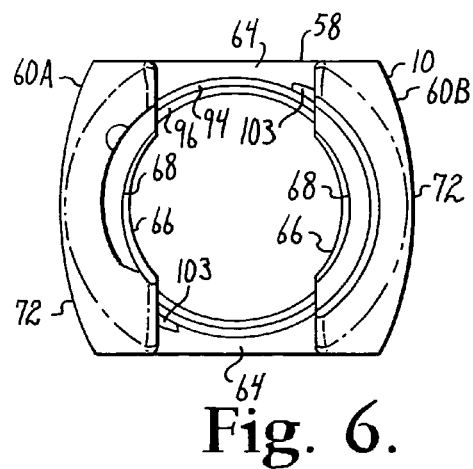
FIG. 6 is an enlarged top plan view of the receiver of FIG. 1.
Figure 7:
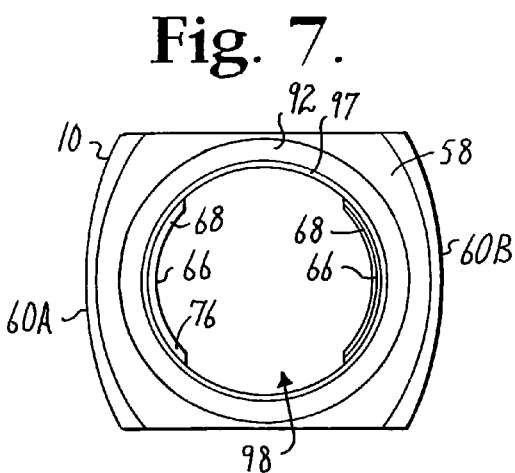
FIG. 7 is an enlarged bottom plan view of the receiver of FIG. 1.
Figure 8:
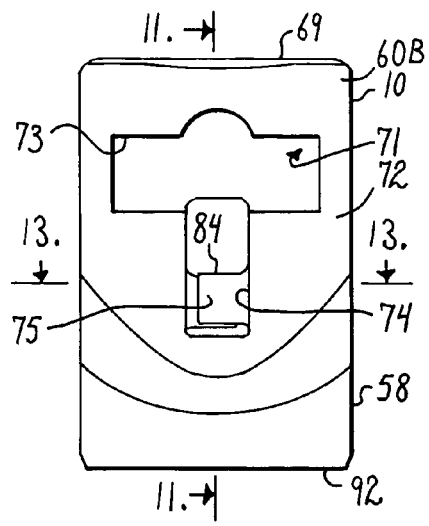
FIG. 8 an enlarged side elevational view of the receiver of FIG. 1.
Figure 9:
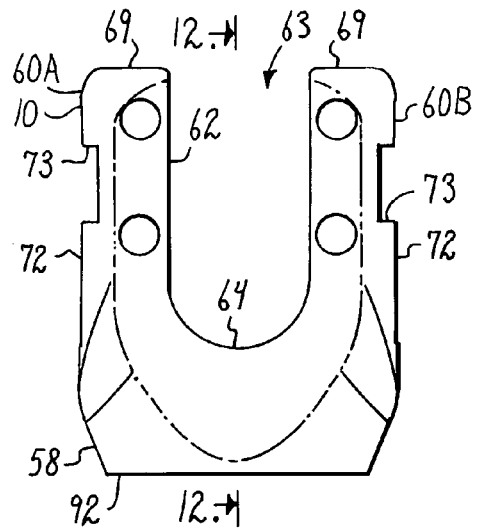
FIG. 9 is an enlarged front elevational view of the receiver of FIG. 1.
Figure 10:
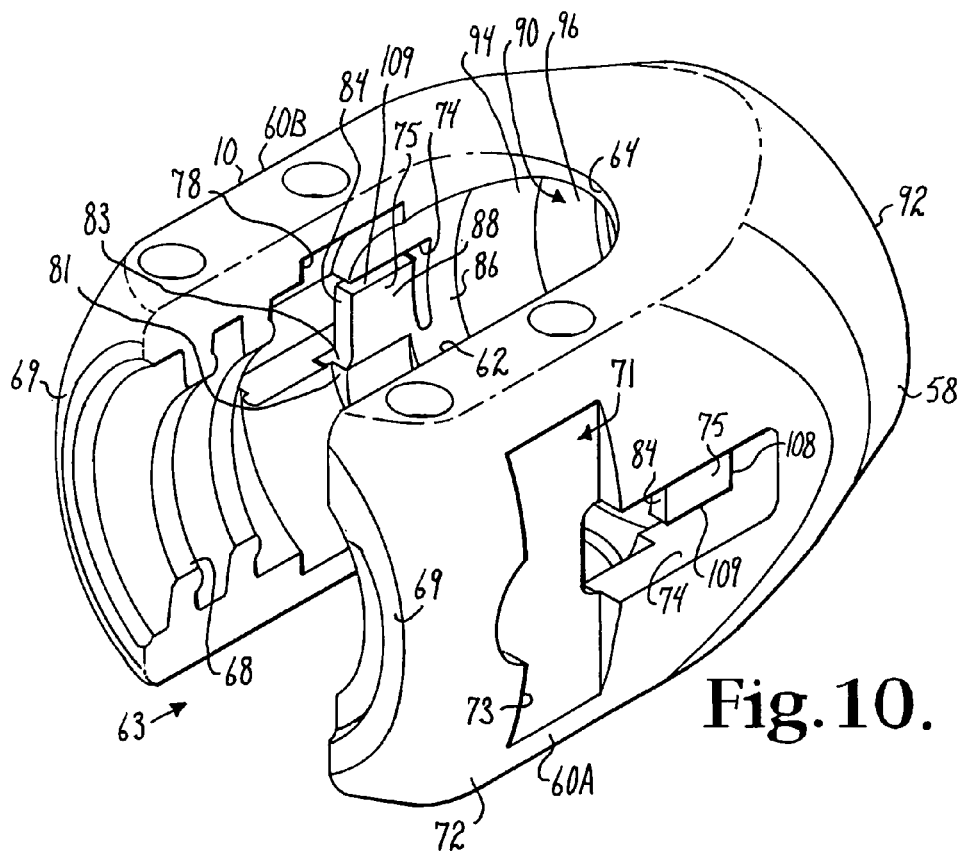
FIG. 10 is an enlarged perspective view of the receiver of FIG. 1.

With reference to FIGS. 1-38 the reference number 1 generally represents a polyaxial bone screw apparatus or assembly according to the present invention. The assembly 1 includes a shank 4, that further includes a body 6 integral with an upwardly extending upper portion or capture structure 8; a receiver 10; a retainer structure 12 and a compression or pressure insert 14. The shank 4, receiver 10, retainer 12 and compression insert 14 are typically factory assembled prior to implantation of the shank body 6 into a vertebra 13, as will be described in greater detail below. FIG. 1 further shows a closure structure 18 of the invention for capturing a longitudinal member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 13. The illustrated rod 21 is hard, stiff, non-elastic and cylindrical, having an outer cylindrical surface 22. It is foreseen (and also will be described with respect to other embodiments) that the rod 21 may be of a different stiffness, elastic, deformable and/or of a different cross-sectional geometry. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The assembly is advantageously configured and factory assembled to provide a surgeon with a bone anchor exhibiting sufficient frictional engagement between the compression insert and the shank upper portion that the shank is positionable to a desired angle with respect to the receiver during and after implantation if the shank and prior to locking of the polyaxial mechanism with the closure structure. In other words, the factory supplied assembly includes a shank that is not floppy or loose with respect to the receiver, allowing greater ease in handling and manipulation during the surgical process. Locking of the insert onto the shank upper portion may also be performed prior to locking with the closure top. Furthermore, inserts according to the invention are advantageously configured to allow for a squeeze release to easily provide for repositioning of the angle of the bone screw shank, as will be described in greater detail below.

The shank 4, best illustrated in FIGS. 1-5, is elongate, with the shank body 6 having a helically wound bone implantable thread 24 (single or dual lead thread form) extending from near a neck 26 located adjacent to the upper portion or capture structure 8, to a tip 28 of the body 6 and extending radially outwardly therefrom. During use, the body 6 utilizing the thread 24 for gripping and advancement is implanted into the vertebra 13 leading with the tip 28 and driven down into the vertebra with an installation or driving tool (not shown), so as to be implanted in the vertebra to near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion 8 that provides a connective or capture apparatus disposed at a distance from the upper end 32 and thus at a distance from the vertebra 13 when the body 6 is implanted in such vertebra.

The shank upper portion 8 is configured for a pivotable connection between the shank 4 (with attached retainer 12) and the receiver 10 prior to fixing of the shank 4 in a desired position with respect to the receiver 10. The shank upper portion 8 has an outer, convex and substantially spherical lower surface 34 that extends outwardly and upwardly from the neck 26 and terminates at a substantially planar ledge or shelf 36 that is annular and disposed perpendicular to the shank axis A. The shelf 36 is sized and shaped to receive and seat the retainer 14 at a bottom surface thereof as will be described in greater detail below. The spherical lower surface 34 has an outer radius that is the same or substantially similar to an outer radius of the retainer 12 as will be described in greater detail below, the surface 34 as well as the retainer 12 outer surface participating in the ball and socket joint formed by the shank 4 and attached retainer 12 within the partially spherical surface defining an inner cavity of the receiver 10. Extending upwardly from the ledge 36 is a cylindrical surface 38, the surface 38 having a radius that is smaller than the radius of the lower spherical surface 34. Extending substantially radially outwardly from the cylindrical surface 38 are three evenly spaced cam projections or lugs 40, each with a lower surface or ledge 41 that faces toward the ledge 36 and is disposed at a slight angle with respect thereto. As will be discussed in greater detail below, the lower ledge 36, cylindrical surface 38 and upper ledges 41 cooperate to capture and fix the retainer 12 to the shank upper portion 8, prohibiting movement of the retainer 12 along the axis A once the retainer 12 is located between the ledges 36 and 41. It is noted that according to the invention, one, two, three or more cam projections 40 may be disposed about the cylindrical surface 38. Each of the projections 40 further include an outer substantially cylindrical surface 42 bounded by opposed side surfaces 43. A partially spherical or domed top surface 44 partially defines each of the projections 40, terminating at the projection surfaces 42 and the cylindrical surface 38 located between each of the cam projections 40. The spherical surface 44 has an outer radius configured for sliding cooperation and ultimate frictional mating with a substantially spherical concave surface of the compression insert 14 that has the same or substantially similar radius as the surface 44. The radius of the surface 44 is smaller than the radius of the lower spherical surface 34. Located near or adjacent to the surface 44 is an annular top surface 46. A counter sunk substantially planar base or seating surface 49 partially defines an internal drive feature or imprint 50. The illustrated internal drive feature 50 is an aperture formed in the top surface 46 and has a hex shape designed to receive a hex tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base 49 of the drive feature 50 is disposed perpendicular to the axis A with the drive feature 49 otherwise being coaxial with the axis A. In operation, a driving tool is received in the internal drive feature 50, being seated at the base 49 and engaging the six faces of the drive feature 50 for both driving and rotating the shank body 6 into the vertebra 13, either before the shank 4 is attached to the receiver 10 or after the shank 4 is attached to the receiver 10, with the shank body 6 being driven into the vertebra 13 with the driving tool extending into the receiver 10.

The shank 4 shown in the drawings is cannulated, having a small central bore 51 extending an entire length of the shank 4 along the axis A. The bore 50 is defined by an inner cylindrical wall of the shank 4 and has a circular opening at the shank tip 28 and an upper opening communicating with the internal drive 50 at the surface 49. The bore 51 is coaxial with the threaded body 6 and the upper portion 8. The bore 51 provides a passage through the shank 4 interior for a length of wire (not shown) inserted into the vertebra 13 prior to the insertion of the shank body 6, the wire providing a guide for insertion of the shank body 6 into the vertebra 13.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 6-13, the receiver 10 has a generally U-shaped appearance with a partially discontinuous substantially cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 13, the axis B is typically disposed at an angle with respect to the axis A, as shown, for example, in FIG. 33.

The receiver 10 includes a partially cylindrical and partially frusto-conical base 58 integral with a pair of opposed upstanding arms 60A and 60B, the arms forming a cradle and defining a U-shaped channel 62 between the arms 60A and B with an upper opening, generally 63, and a U-shaped lower seat 64, the channel 62 having a width for operably snugly receiving the rod 21 between the arms 60A and B. Each of the arms 60A and 60B has an interior surface, generally 66, that has a cylindrical profile and further includes a partial helically wound guide and advancement structure 68 extending radially inwardly from the surface 66 and located adjacent top surfaces 69 of each of the arms 60. In the illustrated embodiment, the guide and advancement structure 68 is a partial helically wound interlocking flangeform configured to mate under rotation with a similar structure on the closure structure 18, as described more fully below. However, it is foreseen that the guide and advancement structure 68 could alternatively be a square-shaped thread, a buttress thread, a reverse angle thread or other thread-like or non-thread-like helically wound discontinuous advancement structure for operably guiding under rotation and advancing the closure structure 18 downward between the arms 60, as well as eventual torquing when the closure structure 18 abuts against the rod 21.

An opposed pair of tool receiving and engaging features, generally 71, are formed on outer surfaces 72 of the arms 60A and 60B. The illustrated features 71 are in a T-shape form and include and upper groove or recess 73 running substantially parallel to the respective top surface 69 that does not extend through the respective arm 60A or 60B and a connecting transverse, substantially rectangular lower recess or through bore 74 that does extend from each arm outer surface 72 to each interior surface 66, providing access to laterally extending spring tabs 75 that bias against the pressure insert 14 to prohibit reverse (illustrated as counter-clockwise) rotational movement of the insert about the receiver axis once the insert is loaded in the receiver 10, as will be described in greater detail below. The aperture feature 71 and alternatively, any additional tool receiving and engaging apertures may be formed in the receiver outer surfaces and used for holding the receiver 10 during assembly with the shank 4, the retainer 12 and the insert 14, during the implantation of the shank body 6 into a vertebra when the shank is pre-assembled with the receiver 10, and during assembly of the bone anchor assembly 1 with the rod 21 and the closure structure 18. It is foreseen that tool receiving grooves or apertures may be configured in a variety of shapes and sizes and be disposed at other locations on the receiver arms 60A and 60B.

Figure 11:
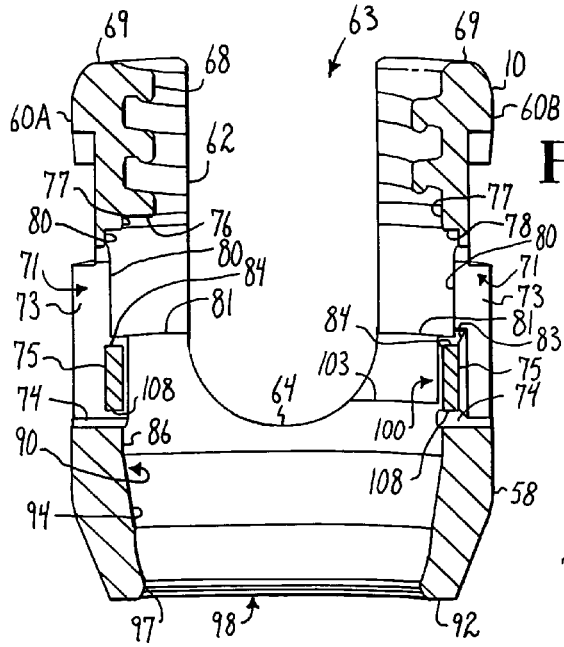
FIG. 11 is an enlarged cross-sectional view taken along the line 11-11 of FIG. 8.

Returning to the interior surface 66 of the receiver arms 60A and 60B, located below the guide and advancement structure 68 on each of the arms is a discontinuous cylindrical surface 77, having a diameter approximately the same as a greater diameter of the guide and advancement structure 68. The space under the guide and advancement structure 68 that is defined in part by the cylindrical surface 77 forms a run-out area for the closure top 18. With particular reference to FIG. 11, on the arm 60A, the cylindrical surface 77 is adjacent to an upper surface or ledge 76 that partially defines the flange form 68 run-out and also serves as an intermediate or temporary abutment feature (along with the cylindrical surface 77) for the insert 14 as shown, for example, in FIG. 34a, and as will be discussed in greater detail below. Adjacent to and located below the cylindrical surface 77 is a discontinuous annular surface 78 that in turn is adjacent to a discontinuous substantially cylindrical surface 80. The surface 80 extends from the surface 78 to an annular lip or ledge 81 that is disposed perpendicular to the axis B and extends radially inwardly toward the axis B. On each arm 60A and 60B, a portion of the ledge 81 is adjacent to and integral with a sloping or curved transition surface 83 that in turn is adjacent to and integral with an upper surface 84 of the respective spring tab 75. Adjacent to the annular lip 81 is another partially discontinuous substantially cylindrical surface 86 that partially defines the arms 60A and 60B as well as extends into the base 58. Thus the surface 86 also partially defines the lower seat 64 of the U-shaped channel 62. An inner surface 88 of the spring tab 75 is integral with the surface 86. The surface 86 has a diameter smaller than the diameter of the cylindrical surface 80, but larger than the diameter of the surface 77; this diameter feature will come into play with respect to the cooperation between the insert 14 and the receiver inner surfaces 76, 77, 78 and 86 as will be described in detail below. As mentioned above, the surface 86 also partially defines an inner cavity, generally 90, of the base 58 of the receiver 10, the cavity 90 and the U-shaped channel 62 defining a through bore of the receiver 10 from the top surface 69 to a bottom surface 92 thereof. Moving downwardly further into the base cavity 90, a substantially conical surface 94 is adjacent to the cylindrical surface 86 and terminates at a radiused or spherical seating surface 96. It is noted that the surface 94 as well as portions of the surface 86 may be partially spherical or otherwise curved in some embodiments of the invention. The surface 96 is sized and shaped for slidably mating with the retainer structure 12 and ultimately frictionally mating therewith as will be described in greater detail below. The spherical seating surface 96 is adjacent a flared surface or as shown, a series of beveled surfaces that provide a neck 97 that forms a bottom opening, generally 98, to the cavity 90 at the receiver bottom surface 92. The neck 97 is sized and shaped to be smaller than an outer radial dimension of the retainer 12 when the retainer 12 is fixed to the shank upper portion 8, so as to form a restriction to prevent the structure 12 and attached shank portion 8 from passing through the cavity 90 and out the lower exterior 92 of the receiver 10 during operation thereof.

Figure 12:
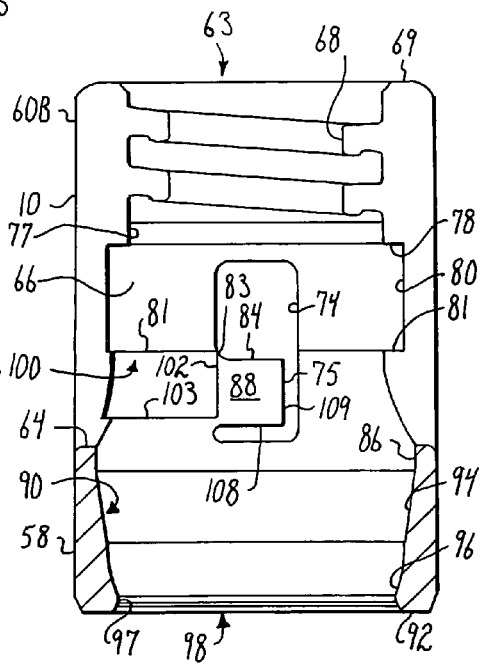
FIG. 12 is an enlarged cross-sectional view taken along the line 12-12 of FIG. 9.
Figure 13:
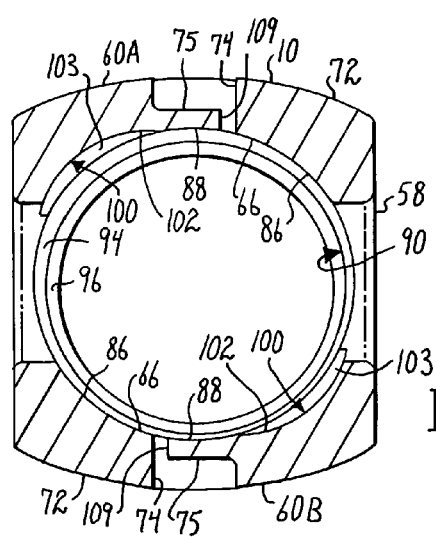
FIG. 13 is an enlarged cross-sectional view taken along the line 13-13 of FIG. 8.
Figure 19:
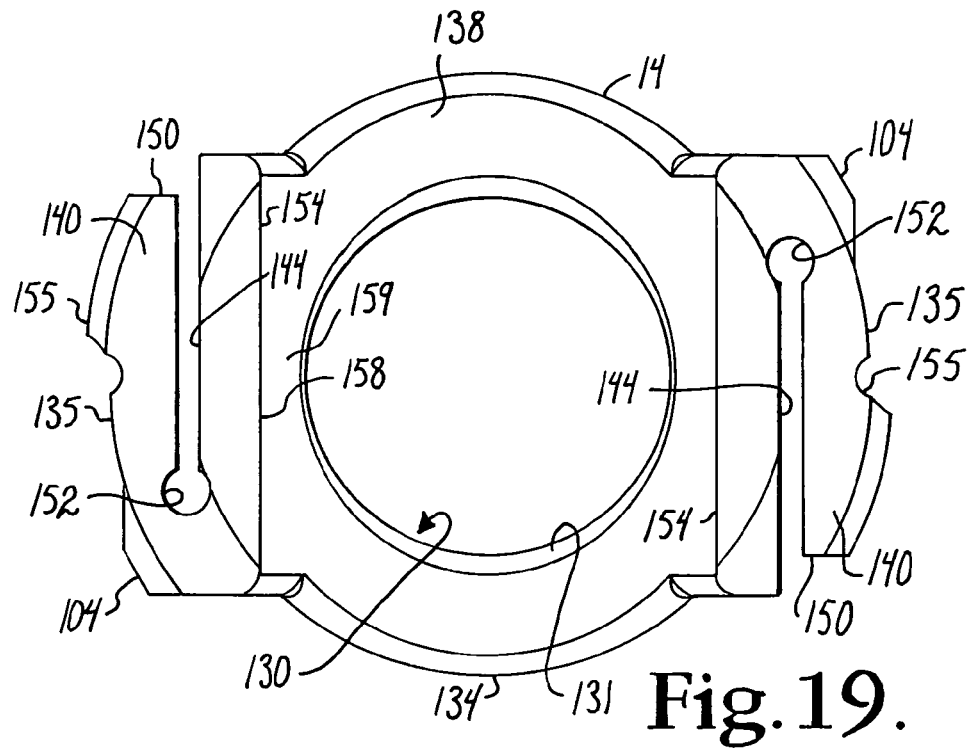
FIG. 19 is an enlarged top plan view of the insert of FIG. 1.
Figure 20:
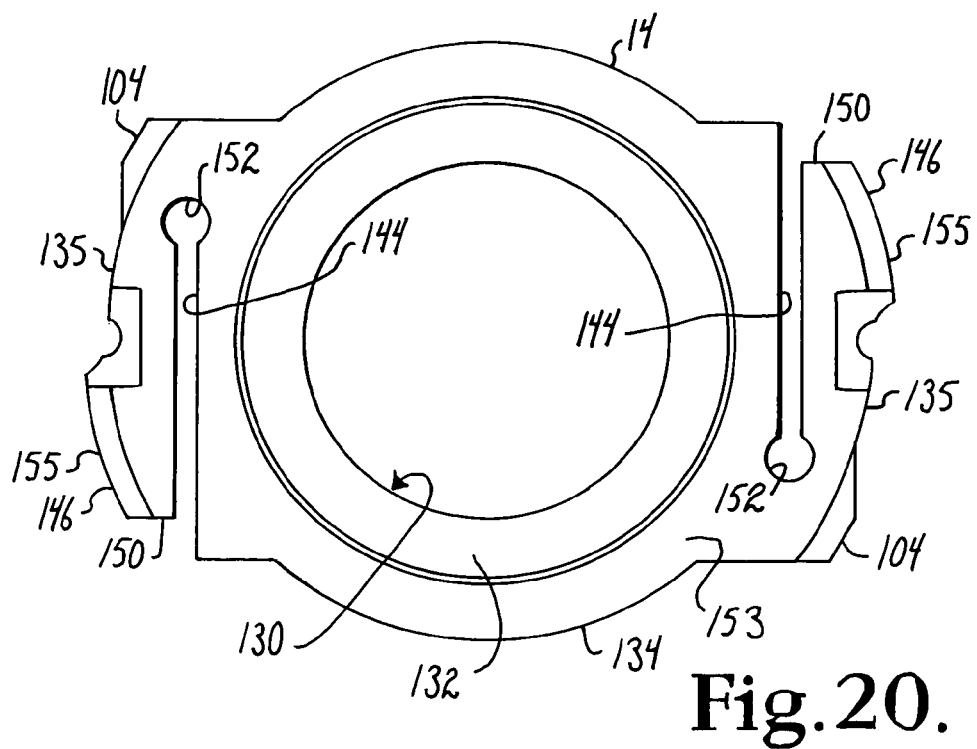
FIG. 20 is an enlarged bottom plan view of the insert of FIG. 1.
Figure 21:
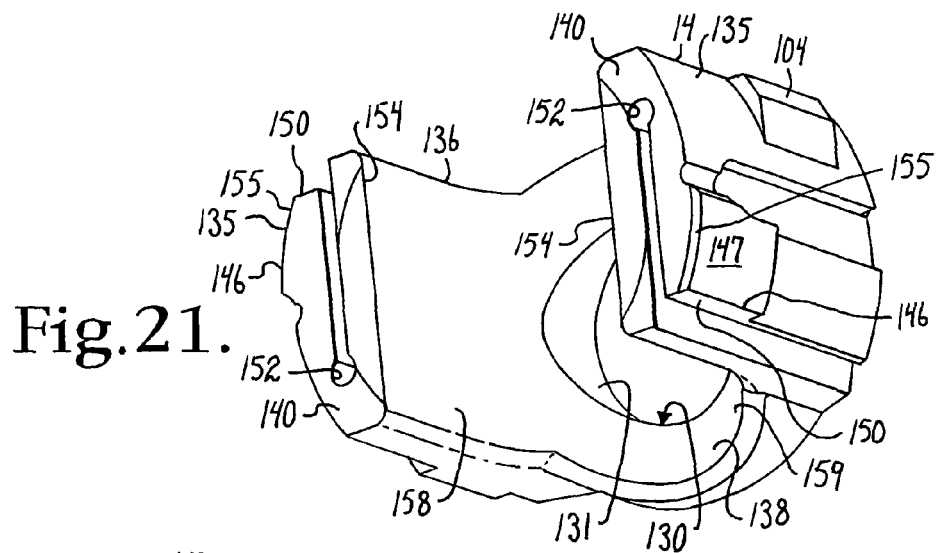
FIG. 21 is an enlarged perspective view of the insert of FIG. 1.
Figure 22:
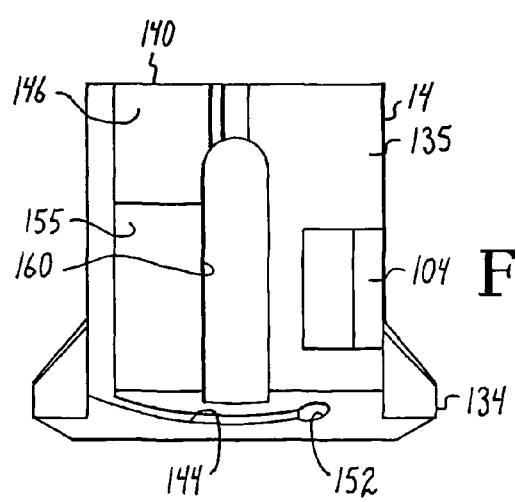
FIG. 22 is an enlarged side elevational view of the insert of FIG. 1.
Figure 23:
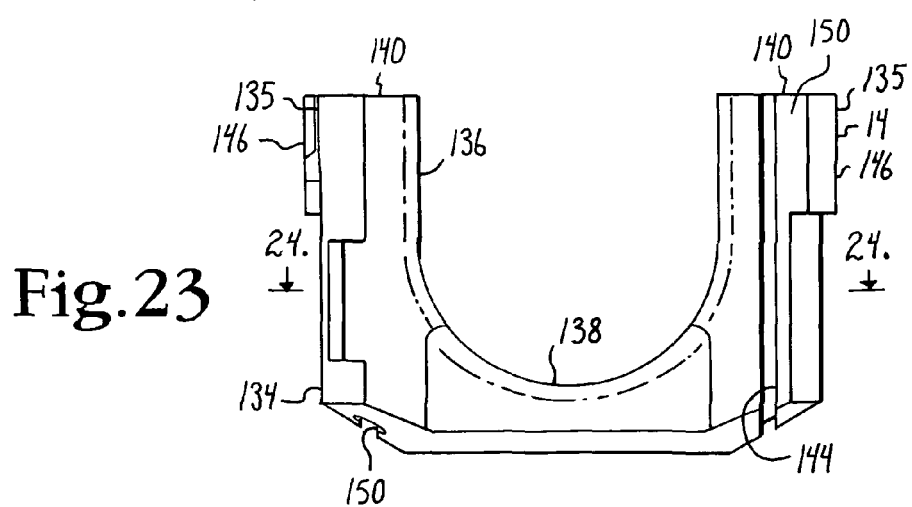
FIG. 23 is an enlarged front elevational view of the insert of FIG. 1.
Figure 24:
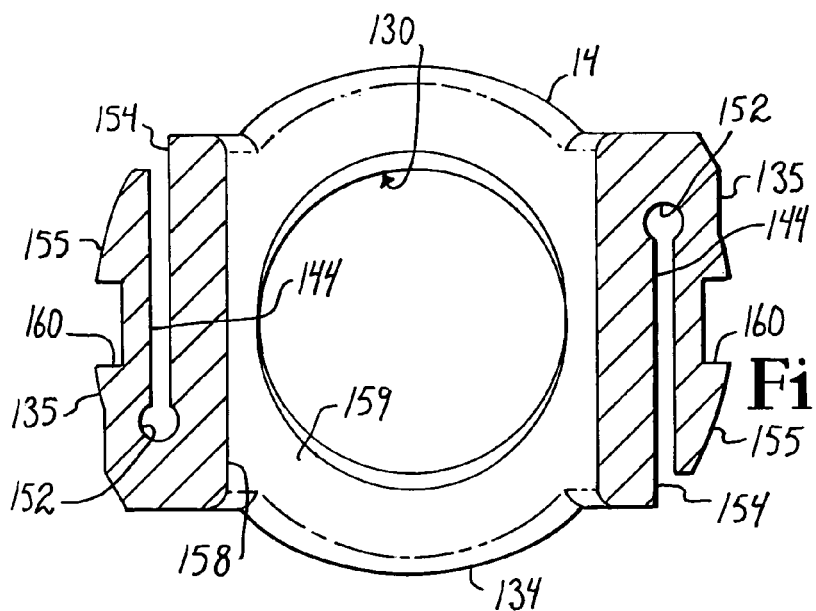
FIG. 24 is an enlarged cross-sectional view taken along the line 24-24 of FIG. 23.

Returning to the surface 86, with reference to FIGS. 12 and 13, and in particular to the surface 86 that extends upwardly into the arms 60A and 60B, formed within each of the substantially cylindrical surfaces 86 and located directly beneath the annular lip 81 is a recess, generally 100, partially defined by a rounded stop or abutment wall 102 and partially defined by a lower annular lip or ledge 103. As will be described in greater detail below, the cooperating compression insert 14 includes a cooperating structure 104 that extends outwardly from each arm thereof that abuts against the respective abutment wall 102 of each of the receiver arms, providing a centering stop or block when the insert 14 is rotated into place in a clockwise manner as will be described below.

Finally, returning to the laterally extending spring tabs 75, that include top surfaces 84 and inner surfaces 88 previously described herein, each spring tab 75 further includes a bottom surface 108 and an end surface 109. The surface 109 is adjacent to and extends between the surfaces 108 and 84, the end surface 109 running substantially parallel to the receiver axis B. The end surfaces 109 of the opposing spring tabs 75 generally face in opposite directions. As described more fully below and shown, for example, in FIG. 31, during assembly, the tabs 75 are pressed radially inwardly to engage the insert 14 and prohibit counter-clockwise motion of the insert 14 with respect to the receiver 10.

With particular reference to FIGS. 1 and 14-18, the retainer 12 that operates to capture the shank upper portion 8 within the receiver 10 has a central axis that is operationally the same as the axis A associated with the shank 4 when the shank upper portion 8 and the retainer 12 are installed within the receiver 10. The retainer 12 is typically made from a hard material, that also may be resilient, such as stainless steel or titanium alloy, for embodiments (not shown) having a slit or slot that would allow for top or bottom loading, so that the retainer 12 may be contracted or expanded during assembly. The retainer structure 12 has a central bore, generally 110, that passes entirely through the retainer structure 12 from a top surface 112 to a bottom surface 114 thereof. The bottom surface 114 is substantially planar and disposed perpendicular to the axis A when the retainer is fixed to the shank 4 with the surface 114 abutting the shank surface 36 as shown, for example, in FIG. 18. The top surface 112 is disposed at an angle with respect to the axis A when the retainer 12 is fixed to the shank 4, the surface 112 sloping radially downwardly to provide space and clearance between the retainer 12 and the insert 14 when the assembly 1 is fully assembled and placed at any angle of inclination of the shank 4 with respect to the receiver 10. A first inner cylindrical surface 116 defines a substantial portion of the bore 110. The cylindrical surface 116 is sized and shaped to be slidingly received about the cylindrical surface portion 38 of the shank upper portion 8. Extending inwardly radially from the surface 116 are three evenly spaced cam projections or shelves 118 sized and shaped to cooperate with the cam projections 40 of the shank upper portion 8 for fixing the retainer 12 to the shank upper portion 8. The cam shelves 118 extend from at or near the retainer bottom 114 to a location spaced from the retainer top 112. The cam shelves 118 are sized and shaped to provide direct mating support with each shank projection 40. The cam shelves 118 are also spaced from the top surface 112 to provide adequate space for loading rotation and placement of the cam projections 40 of the shank upper portion 8 with respect to the retainer 12 during assembly within the receiver 10 of the bone screw 1. Each of the illustrated cam shelves 118 includes an upper, sloping or slanted seating surface 120 and an opposed bottom surface 122 that is flush and integral with the bottom surface 114 of the retainer 12. The illustrated camming seating surfaces 120 are each disposed about midway between the top 112 and the bottom 114 of the retainer 12, but may be located slightly higher or lower along the surface 116. Each camming shelf 118 further includes opposed side surfaces 124 and 125 running from the bottom surface 114 to the seating surface 120. Each of the surfaces 124 and 125 are curved and substantially concave. Each shelf includes an inner cylindrical surface 126 sized and shaped to slidingly mate with the surfaces 42 of the cam projections 40 of the shank upper portion 8. The sloping seating surfaces 120 are sized to receive the lugs or projections 40 at the surfaces 41 thereof, with the surfaces 36 and 41 of the shank upper portion forming a cam track between which each camming shelf 118 slides and is captured and frictionally fixed. A degree of inclination of the surface 120 substantially matches a degree of inclination of the bottom surface 41 of the lug 40. In the illustrated embodiment, the degree of inclination is about three degrees, but it is foreseen that it may be more or less than that illustrated. In some embodiments according to the invention, one or both the ramped surfaces 41 and 120 include a roughening, ridges or some other treatment to further aid frictional locking of the retainer 12 with respect to each lug 40. Furthermore, in some embodiments of the invention, fixing engagement between the lugs 40 and the shelves 122 may be enhanced by a weld or adhesive. For example, the illustrated camming shelves 118 are slightly wider than the shank projections 40 at the side surfaces 124 and 125 so as to advantageously accommodate a spot weld or other fixing or adhering structure or substance.

The retainer 12 also has a radially outer partially spherically shaped surface 129 sized and shaped to mate with the partial spherical shaped seating surface 96 of the receiver 10. The surface 129 includes an outer radius that is larger than a radius of the lower opening 98 of the receiver 10, thereby prohibiting the retainer 12 and the shank upper portion 8 from passing through the opening 98 once the retainer 12 is fixed to the shank upper portion 8 within the receiver cavity 90. Although not required, it is foreseen that the outer partially spherically shaped surface 129 may be a high friction surface such as a knurled surface or the like.

With particular reference to FIGS. 1 and 19-24, the compression or pressure insert 14 is illustrated that is sized and shaped to be received by and down-loaded into the receiver 10 through the channel opening 66 as illustrated in FIGS. 29-31. The compression insert 14 has an operational central axis that is the same as the central axis B of the receiver 10. The compression insert 14 has a central channel or through bore, generally 130, substantially defined by an inner substantially cylindrical surface 131 coaxial with an inner partially spherical surface 132. The compression insert 14 through bore is sized and shaped to receive a driving tool (not shown) therethrough that engages the shank drive feature 50 when the shank body 6 is driven into bone with the receiver 10 attached. The surface 132 is sized and shaped to slidingly receive and ultimately frictionally engage the substantially spherical or domed surface 44 of the shank upper portion 8 such that the surface 44 initially frictionally slidingly and pivotally mates with the spherical surface 132 to create a ball-and-socket type joint. The surfaces 44 and/or 132 may include a roughening or surface finish to aid in frictional contact between them once a desired angle of articulation of the shank 4 with respect to the receiver 10 is reached.

The compression insert 14 includes a substantially cylindrical base body 134 integral with a pair of upstanding arms 135. The bore 130 is disposed primarily within the base body 134 and communicates with a generally U-shaped through channel 136 that is defined by the upstanding arms 135. The channel 136 has a lower seat 138 sized and shaped to closely, snugly engage the rod 21. It is foreseen that an alternative embodiment may be configured to include planar holding surfaces that closely hold a square or rectangular bar as well as hold a cylindrical rod-shaped or corded longitudinal connecting member. The arms 135 disposed on either side of the channel 136 extend outwardly and upwardly from the body 134. The arms 135 are sized and configured for ultimate placement near the run-out below the receiver guide and advancement structure 68. It is foreseen that in some embodiments of the invention, the arms may be extended and the closure top configured such the arms ultimately directly engage the closure top for locking of the polyaxial mechanism. In the present embodiment, the arms 135 include top surfaces 140 that are ultimately positioned in spaced relation with the closure top 18, so that the closure top 18 frictionally engages and holds the rod 21, pressing the rod 21 downwardly against the seating surface 138, the insert 14 in turn pressing against the domed top 44 of the shank 4 to lock the polyaxial mechanism of the bone screw assembly 1. The illustrated insert 14 further includes features that allow for a non-floppy frictional fit between the insert and the shank 4 during assembly and also for a locking of the insert 14 with respect to the shank 4 prior to locking down of the closure top 18. These features include a key-hole like through slot 144 disposed within each arm 135 running substantially vertically from the top surface 140 and through the base body 134. Furthermore, each arm 135 includes at least one radially projected upper portion 146 with an outer partially cylindrical surface 147 for engaging with the receiver 10 as will be described more fully below. It is foreseen that inserts 14 according to the invention may have at least one and up to a plurality of such portions 146. The illustrated slots 144 open along opposed side surfaces 150 of the arms, the side surfaces 150 each also defining a portion of one of the projected upper portions 146. Each slot 144 terminates at a cylindrical through bore 152 that also runs from the top surface 140 through the base body 134 and out a base surface 153, the bore 152 being spaced from inner and outer surfaces of each of the arms 135. Each slot 144 separates each arm 135 into an inner arm portion 154 and an outer arm portion 155 that includes the respective projected upper portion 146, the portions 155 being compressible towards the portions 154 during assembly of the insert 14 within the receiver 10 as will be described in greater detail below. Each arm 135 further includes inner planar walls 158 and inner sloping lower surfaces 159. Each outer arm portion 155 further includes a generally vertically extending recess or partial aperture 160 sized and shaped to receive holding tabs 75, or, in some embodiments of the invention, crimped material from the receiver.

The pressure insert body 134 located between the arms 135 has an outer diameter slightly smaller than a diameter between crests of the guide and advancement structure 68 of the receiver 10 allowing for top loading of the compression insert 14 into the receiver opening 63, with the arms 135 of the insert 14 being located between the receiver arms 60A and 60B during insertion of the insert 14 into the receiver 10. Once located between the guide and advancement structure above and the shank upper portion 8 below, the insert 14 is rotated into place about the receiver axis until the arms 135 are directly below the guide and advancement structure 68 as will be described in greater detail below. At some point in the assembly, a tool (not shown) may be inserted into the receiver apertures, to press the tabs 75 into the insert recesses 160. It is noted that assembly of the shank 4 with the retainer 12 within the receiver 10, followed by insertion of the lower compression insert 14 into the receiver 10 are assembly steps typically performed at the factory, advantageously providing a surgeon with a polyaxial bone screw with the lower insert 14 already held in alignment with the receiver 10 and providing a non-floppy, but pivotable shank ready for insertion into a vertebra. The compression or pressure insert 14 ultimately seats exclusively on the surface 44 of the shank upper portion 8, with the base surface 153 sloping upwardly and away from the shank upper portion 8, providing clearance between the retainer 12 and the insert 14 during pivoting of the shank 4 with respect to the receiver 10. The assembly may be configured so that the insert 14 extends at least partially into the receiver U-shaped channel 62.

With reference to FIGS. 1 and 35-38, the illustrated elongate rod or longitudinal connecting member 21 can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials.

Longitudinal connecting members for use with the assembly 1 may take a variety of shapes, including but not limited to rods or bars of oval, rectangular or other curved or polygonal cross-section. The shape of the insert 14 may be modified so as to closely hold, and if desired, fix or slidingly capture the longitudinal connecting member to the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector May be a component of a longer overall dynamic stabilization connecting member, with cylindrical or bar-shaped portions sized and shaped for being received by the compression insert 14 of the receiver having a U-shaped channel (or rectangular- or other-shaped channel) for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 36-38, the closure structure or closure top 18 shown with the assembly 1 is rotatably received between the spaced arms 60A and 60B. It is noted that the closure 18 can be any of a variety of different types of closure structures for use in conjunction with the present invention with suitable mating structure on the upstanding arms 60A and 60B. It is also foreseen that the closure top could be a twist-in or slide-in closure structure. The illustrated closure structure 18 is substantially cylindrical and includes an outer helically wound guide and advancement structure 162 in the form of a flange form that operably joins with the guide and advancement structure 68 disposed on the arms 60A and 60B of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 18 downward between the arms 60A and 60B and having such a nature as to resist splaying of the arms when the closure structure 18 is advanced into the U-shaped channel 62. The illustrated closure structure 18 also includes a top surface 164 with an internal drive 166 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 166 is used for both rotatable engagement and, if needed, disengagement of the closure 18 from the receiver arms 60A and 60B. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 168 of the closure is planar and further includes a point 169 and a rim 170 for engagement and penetration into the surface 22 of the rod 21 in certain embodiments of the invention. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 60A and B.

Figure 25:
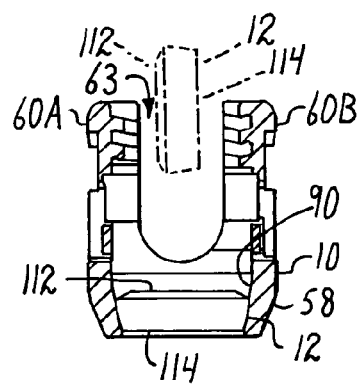
FIG. 25 is a front elevational view of the receiver and retainer of FIG. 1 with portions broken away to show the detail thereof and further showing a stage of assembly of the retainer in phantom.
Figure 26:
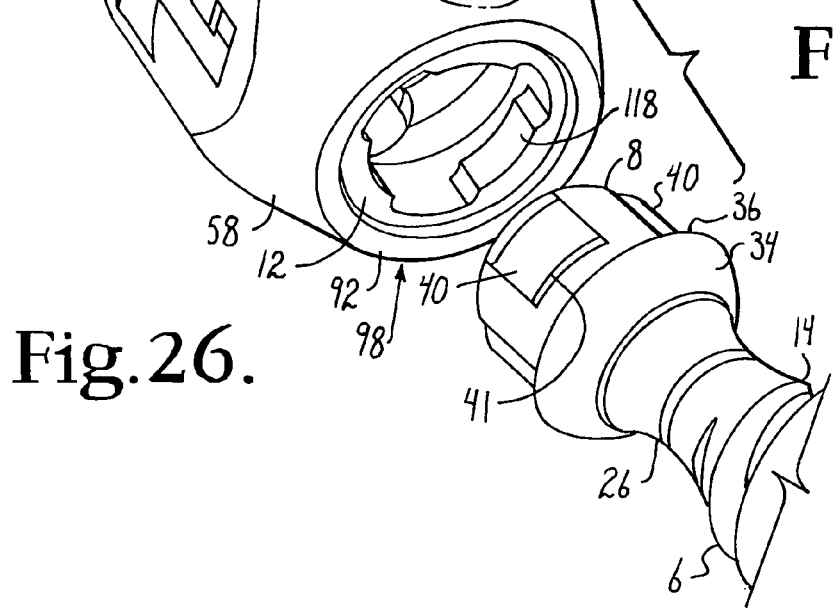
FIG. 26 is an enlarged and partial perspective view of the receiver, retainer and shank of FIG. 1 shown in an early stage of assembly.
Figures 27, 28:
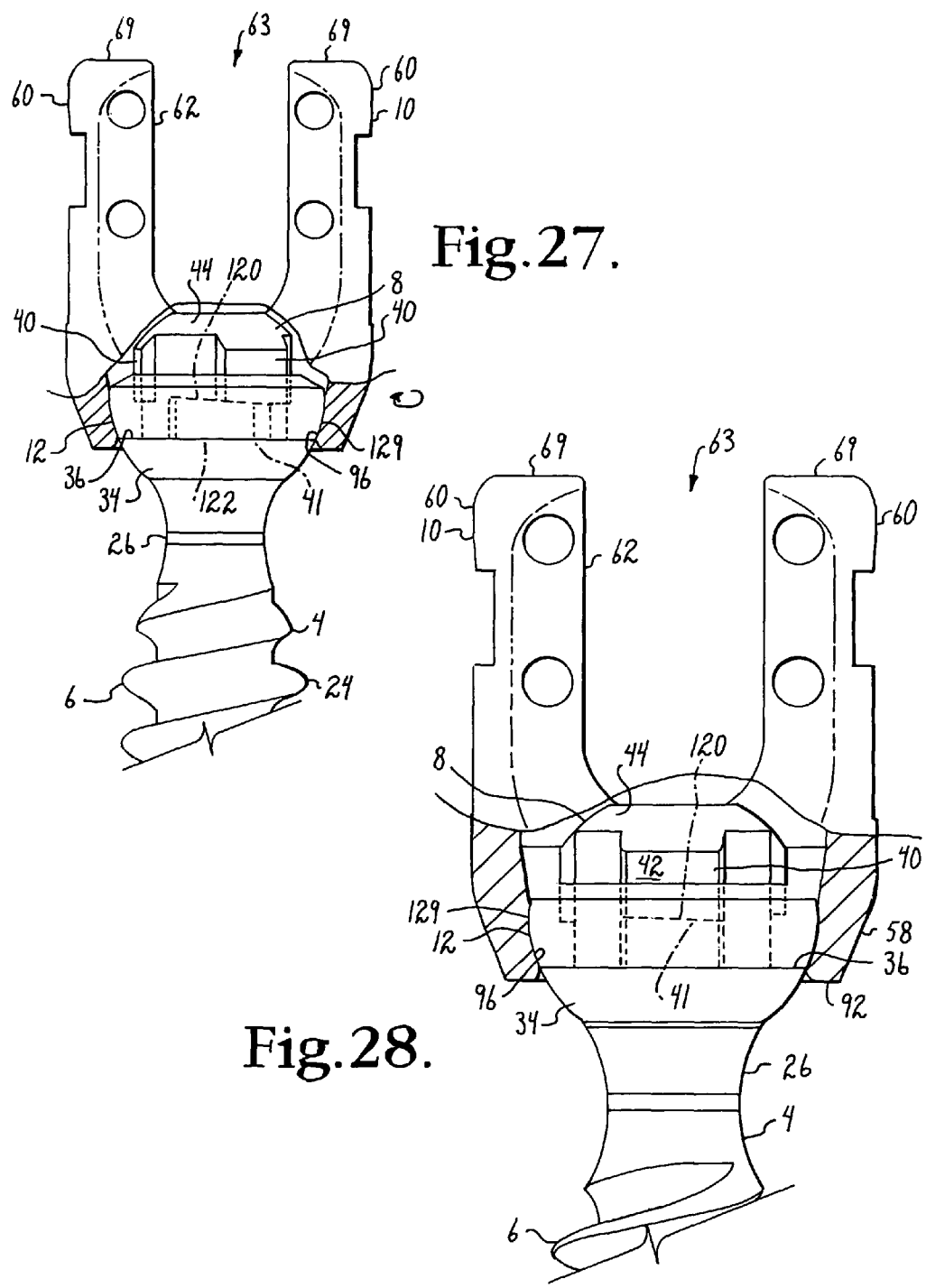
FIG. 27 is an enlarged and partial front elevational view of the receiver, retainer and shank of FIG. 1 shown in a stage of assembly subsequent to that shown in FIG. 26, with portions broken away to show the detail thereof and further showing cooperating portions of the shank and retainer in phantom.
FIG. 28 is an enlarged and partial front elevational view of the receiver, retainer and shank of FIG. 1 shown in a stage of assembly subsequent to that shown in FIG. 27, with portions broken away to show the detail thereof and further showing cooperating portions of the shank and retainer in phantom.

Preferably, the shank 4, receiver 10, the retainer 12 and the compression insert 14 are assembled at a factory setting that includes tooling for holding and alignment of the component pieces and compressing arm portions of the insert 14. Assembly of the shank 4, the receiver 10, the retainer 12 and the compression insert 14 is shown in FIGS. 25-34b. With particular reference to FIG. 25, the ring-like retainer 12 is typically first inserted or top-loaded through the opening 63 with the top 112 and bottom 114 surfaces aligned with the receiver axis B within the receiver U-shaped channel 62 and then into the cavity 90 to dispose the structure 12 within the receiver base 58. Then, the retainer structure 12 is rotated approximately 90 degrees so as to be coaxial with the receiver 10 and then seated in sliding engagement with the seating surface 96 of the receiver 10. With reference to FIGS. 26-28, the shank capture structure 8 is then inserted or bottom-loaded into the receiver 10 through the opening 98. The retainer structure 12, now disposed in the receiver 10 is coaxially aligned with the shank capture structure 8 so that the camming lugs 40 are received by the retainer 12 and moved between and through the camming shelves 118 until the bottom surface 114 of the retainer 12 engages the surface 36 of the shank upper portion 8. The retainer 12 is then partially rotated about the axis A of the shank 4 until the retainer shelves 118 are received in the cam track formed by the shank surface 36 and the shank projection camming or sloped surface 41. With reference to FIGS. 27 and 28, as the retainer 12 is rotated, the shank projection bottom surface 41 frictionally engages the ramped surface 120 of the camming shelf 118, creating a press fit between the surfaces and frictionally locking the retainer 12 between the lugs or projections 40 and the shank upper portion 8 seat 36, the retainer 12 now in fixed coaxial relationship with the shank 4. Preferably, the shank 4 and or the retainer 12 are partially rotated to fully mate such structures at a factory setting that includes tooling for holding and precisely rotating the shank 4 and/or the retainer 12 until locking frictional engagement therebetween is accomplished. Although not shown, it is noted that the retainer structure 12 may also have tooling features, such as a pair of small apertures so that the retainer 12 is also securely held during the rotation with respect to the shank 4. Permanent, rigid engagement of the capture structure 8' to the retainer structure 12 may be further supported by the use of adhesive, a spot weld, a deformation, or the like. At this time both the shank 4 and the retainer 12 are in loose, rotatable and swivelable engagement with the receiver 10, while the shank upper portion 8 and the lower aperture or neck 97 of the receiver 10 cooperate to maintain the shank body 6 in swivelable relation with the receiver 10. Only the retainer 12 is in slidable engagement with the receiver spherical seating surface 96. The shank upper end 44 and the shank body 6 are in spaced relation with the receiver 10. The shank body 6 can be rotated through a substantial angular rotation relative to the receiver 10, both from side to side and from front to rear so as to substantially provide a universal or ball joint.

With reference to FIGS. 29-34b, the compression insert 14 is downloaded into the receiver 10 through the upper opening 63 with the insert bottom surface 153 facing the receiver arm top surfaces 69 and the insert arms 135 located between the receiver arms 60A and 60B. The insert 14 is lowered toward the channel seat 64 until the insert 14 is located below the surface run-out feature 76 of the guide and advancement structure 68 and the spherical surface 132 engages the domed surface 44 of the shank 4. Thereafter, the insert 14 is rotated in a clockwise manner as indicated by the arrow CL in FIG. 30 until the stop structures 104 of the insert 14 abut against the wall 102 of the recess stop 100 located on the receiver arms 60A and 60B (see FIG. 31). During such rotation, the upper projections 146 also engage the receiver cylindrical surface 77, compressing the outer arm portions 155 toward the inner arm portions 154 to provide a slidable friction fit between the insert 14 and the receiver 10 at the surface 77. At this time, the insert 14 engages the shank upper portion 8 at the surface 44 in a manner that allows for pivoting of the shank with respect to the receiver 10 with effort, thus a frictional fit that advantageously allows for setting a desired angle of the shank 4 with respect to the receiver 10, that may be adjusted, but is not otherwise floppy or loosely movable. The surface 76 of the receiver prohibits the insert 14 from moving upwardly away from the shank surface 44. With further reference to FIG. 31, at this time, the spring tabs 75 may be pressed inwardly into the insert recesses 160, preventing counter-clockwise movement of the insert 14 with respect to the receiver 10. FIG. 34a best illustrates the position of the insert 14 with respect to the receiver 10 prior to implanting of the shank body 6 into the vertebra 13.

Figure 32:
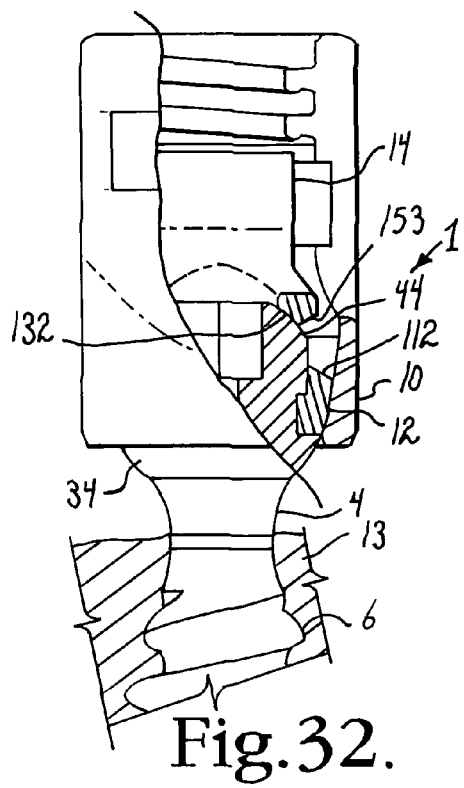
FIG. 32 is a reduced side elevational view of the receiver, retainer, shank and insert of FIG. 31 with portions broken away to show the detail thereof.
Figure 33:
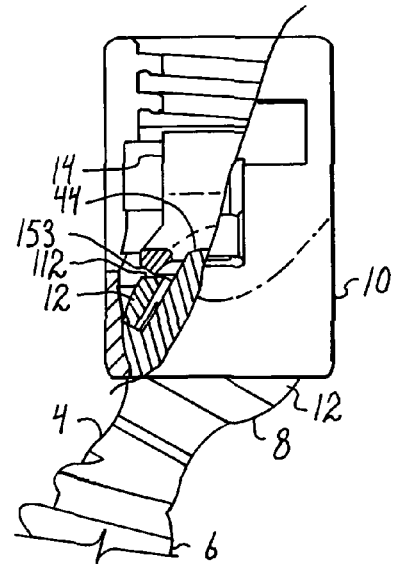
FIG. 33 is a reduced side elevational view, with portions broken away, similar to FIG. 32, further showing the shank pivoted at an angle with respect to the receiver.

With reference to FIG. 32, the assembly 1 made up of the assembled shank 4, receiver 10, retainer 12 and compression insert 14 is screwed into a bone, such as the vertebra 13, by rotation of the shank 4 using a suitable driving tool (not shown) that operably drives and rotates the shank body 6 by engagement thereof at the internal drive 50. Specifically, the vertebra 13 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw assembly is threaded onto the guide wire utilizing the cannulation bore 51 by first threading the wire into the opening at the bottom 28 and then out of the top opening at the drive feature 50. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires. At this time, the receiver 10 may be articulated to a desired position with respect to the shank 4 as shown, for example, in FIG. 33.

Figure 35:
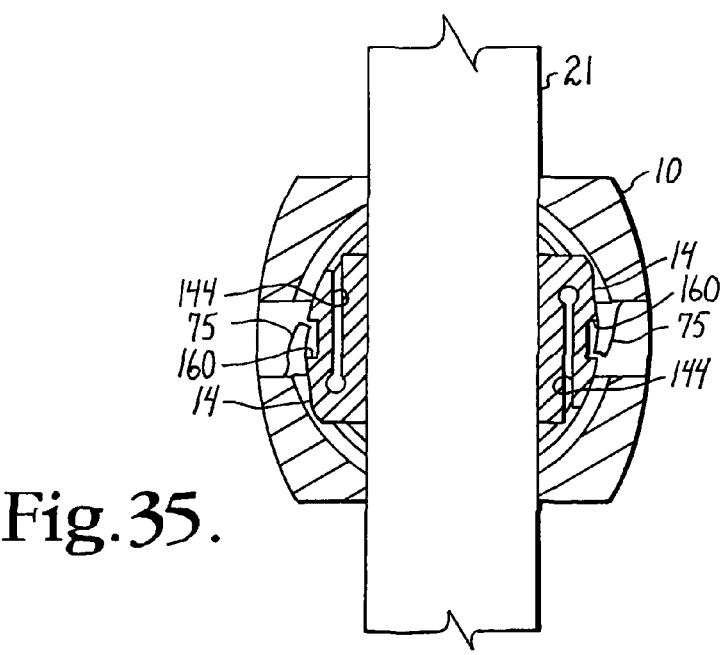
FIG. 35 is a top plan view of the assembly of FIG. 34, with portions broken away to show the detail thereof and further shown with the rod of FIG. 1, the insert being pressable downwardly into the second or locked position by the rod.
Figures 34A, 34B:
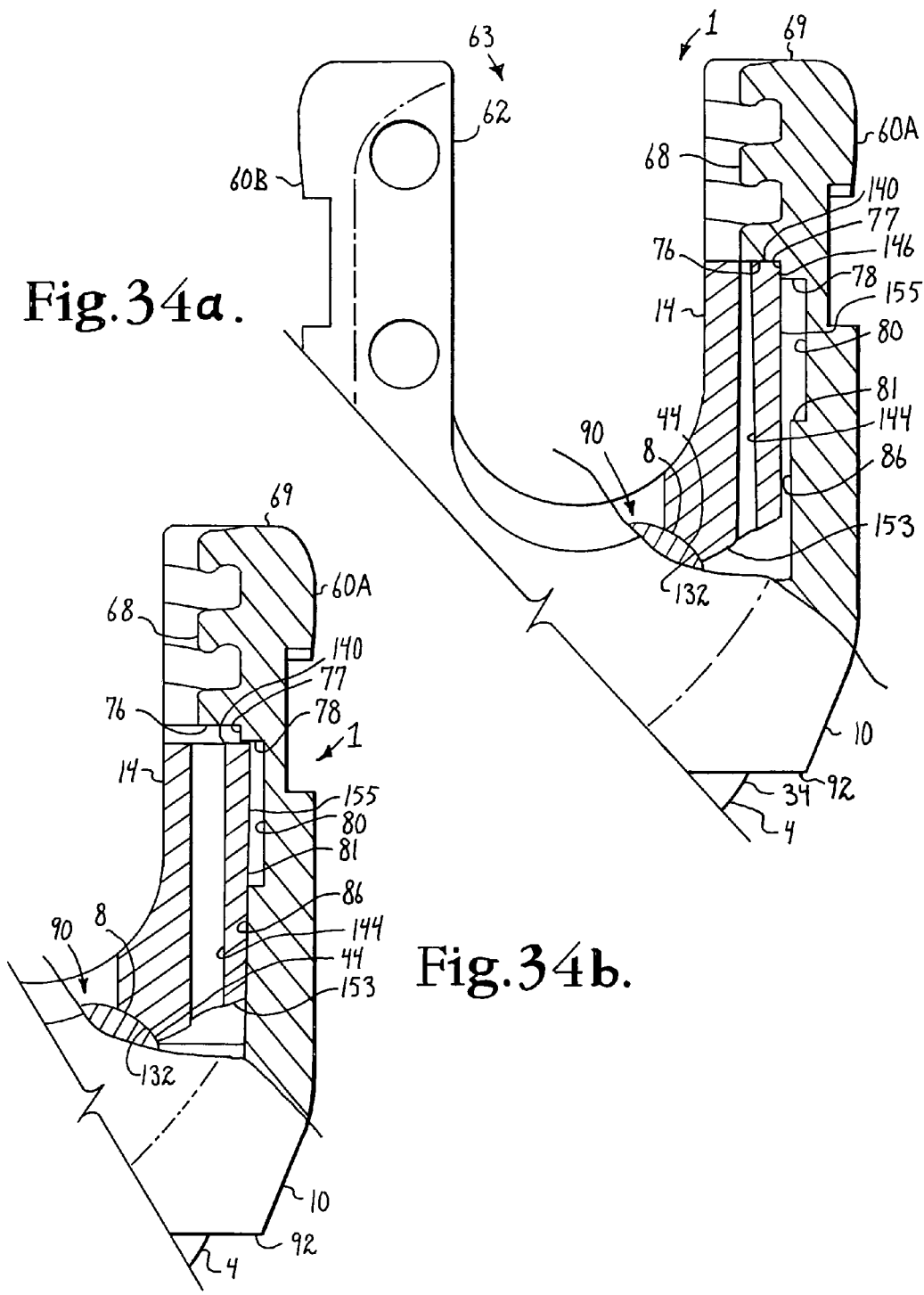
FIG. 34a is an enlarged and partial rear elevational view of the assembly of FIG. 32 with portions broken away to show the detail thereof, the insert being shown in the factory assembled position.
FIG. 34b is an enlarged and partial rear elevational view of the assembly of FIG. 33 with portions broken away to show the detail thereof, the insert being shown in a subsequent second or locked position with respect to the receiver.

With reference to FIGS. 34a, 34b and also FIG. 35, at this time, the insert 14 may be placed into a fixed or locked position with respect to the receiver 10 by pressing the insert 14 axially downwardly against the shank top surface 44. This may be done by pressing the rod 35 into the insert 14 as shown in FIG. 35 or by tooling (not shown) that lowers the insert 14 to a location out of engagement with the cylindrical surface 77 as shown in FIG. 34b. At such time, the outer arm portion 155 resiliently moves or springs back toward a neutral position, and such action puts the outer arm portion 155 into a full, frictional engagement with the lower receiver surface 86, locking the insert 14 against the shank upper portion 8, the shank 4 no longer movable with respect to the receiver 10. At this time the surgeon may make other adjustments in the rod 21 or other longitudinal connection assembly components with confidence that the shank 4 and the receiver 10 of the assembly 1 is fully locked into a desired angular position. If, however, an adjustment is desired, tools (not shown) may be inserted into the receiver aperture 74 and the insert outer arm portion 155 may be compressed inwardly radially toward the axis B, loosening the insert 14 from the receiver cylindrical surface 86, and thus loosening engagement between the insert surface 132 and the shank upper portion surface 44.

Figure 36:
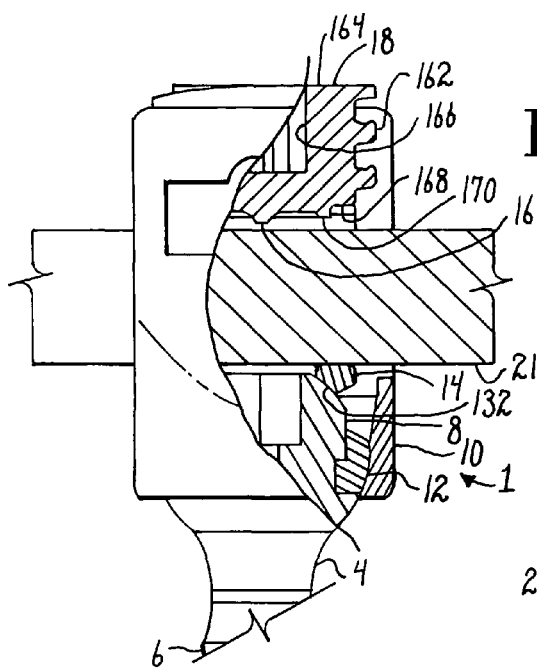
FIG. 36 is an enlarged and partial side elevational view of the assembly of FIG. 35, further showing the closure top of FIG. 1 in a stage of assembly with the receiver with portions broken away to show the detail thereof.
Figure 37:
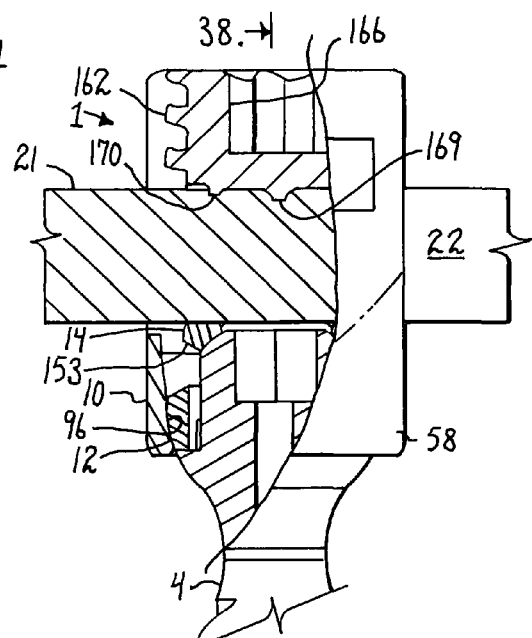
FIG. 37 is an enlarged and partial side elevational view of the assembly of FIG. 36 with portions broken away to show the detail thereof and showing the closure top engaging the rod.
Figure 38:
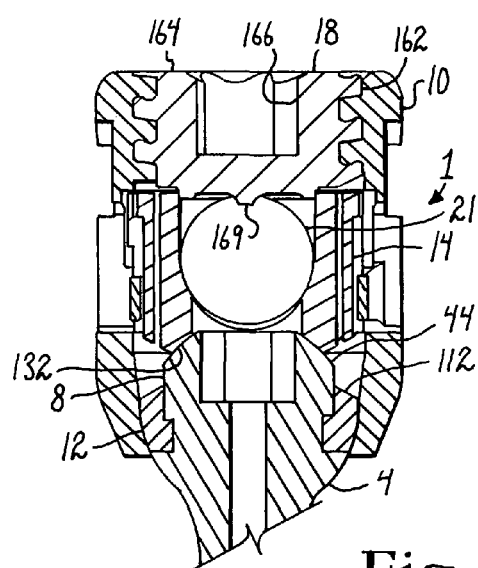
FIG. 38 is an enlarged and partial cross-sectional view taken along the line 38-38 of FIG. 37.

With reference to FIGS. 36-38, the rod 21 is eventually positioned in an open or percutaneous manner in cooperation with the at least two bone screw assemblies 1. The closure structure 18 is then inserted into and advanced between the arms 60A and 60B of each of the receivers 10. The closure structure 18 is rotated, using a tool engaged with the inner drive 166 until a selected pressure is reached at which point the rod 21 engages the insert 14, biasing the insert spherical surface 132 against the shank spherical surface 44.

As the closure structure 18 rotates and moves downwardly into the respective receiver 10, the point 169 and rim 170 engage and penetrate the rod surface 22, the closure structure 18 pressing downwardly against and biasing the rod 21 into engagement with the insert 14 that urges the shank upper portion 8 toward the retainer 12 and into locking engagement therewith, the retainer 12 frictionally abutting the surface 96. For example, about 80 to about 120 inch pounds of torque on the closure top may be applied for fixing the bone screw shank 6 with respect to the receiver 10.

If removal of the rod 21 from any of the bone screw assemblies 1 is necessary, or if it is desired to release the rod 21 at a particular location, disassembly is accomplished by using the driving tool (not shown) that mates with the internal drive 166 on the closure structure 18 to rotate and remove such closure structure from the cooperating receiver 10. Disassembly is then accomplished in reverse order to the procedure described previously herein for assembly.

Figure 39:
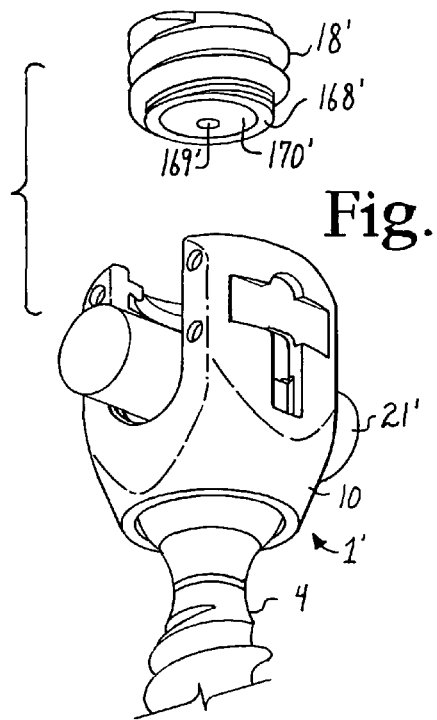
FIG. 39 is an enlarged and partial, partially exploded perspective view of the assembled receiver, shank, retainer and insert of FIGS. 32-34 further shown with an alternative deformable rod and an alternative closure top.
Figure 40:
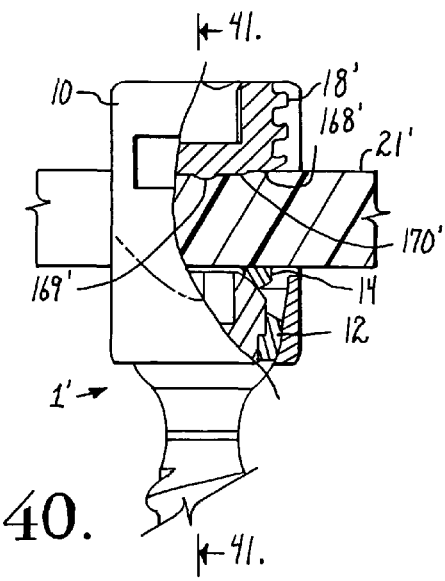
FIG. 40 is a partial side elevational view of the assembly of FIG. 39, shown fully assembled and with portions broken away to show the detail thereof.
Figure 41:
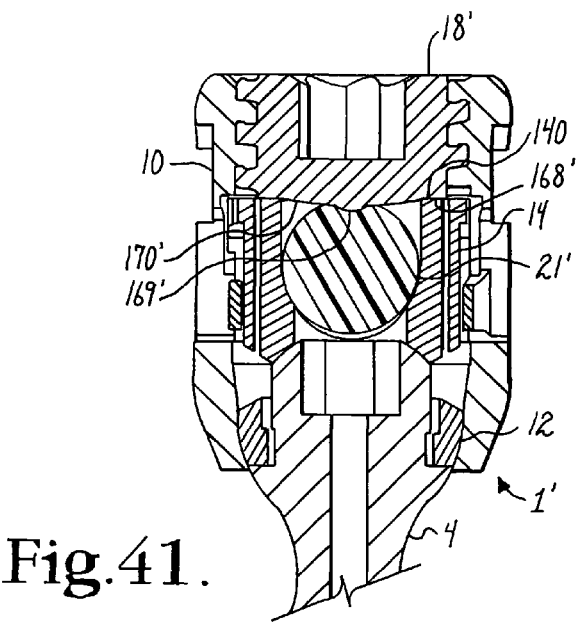
FIG. 41 is an enlarged and partial cross-sectional view taken along the line 41-41 of FIG. 40.

With reference to FIGS. 39-41, the assembly 1 is illustrated with an alternative rod 21' and an alternative closure top 18', thus the resulting assembly is identified as an assembly 1'. The rod 21' is substantially similar to the rod 21 in size and shape. However, the rod 21' is made from a deformable material, illustrated as a plastic material. The closure top 18' is substantially similar to the top 18 with the exception that the top 18' includes an outer annular flat bottom surface 168' adjacent to an otherwise curved bottom that further includes a central rounded point or projection 169' located on a spherical or domed shape surface 170'. As best shown in FIG. 41, when assembled, the closure top surface 168' engages the insert arm top surfaces 140, pressing the insert 14 in a downward direction toward the shank upper portion 8, providing locking of the insert 14 against the shank top surface 44 independent of any engagement between the closure top 18' and the rod 21'. The closure top surfaces 169' and 170' engage and penetrate the deformable rod 21'.

Figure 42:
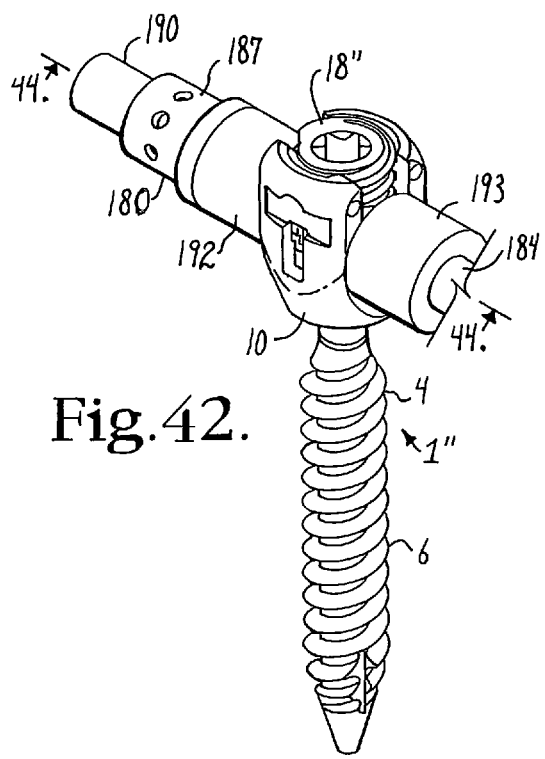
FIG. 42 is a reduced and partial perspective view showing the assembled receiver, shank, retainer and insert of FIGS. 32-34 with a cord, first and second spacers located on either side of the receiver, a threaded connecter, a rod and a closure top configured for slidable engagement with the cord.
Figure 43:
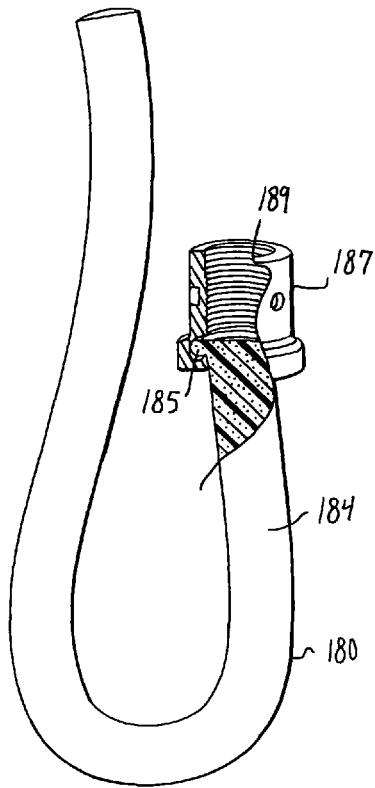
FIG. 43 is a perspective view of the cord and connector of FIG. 42 with portions broken away to show the detail thereof.
Figure 44:
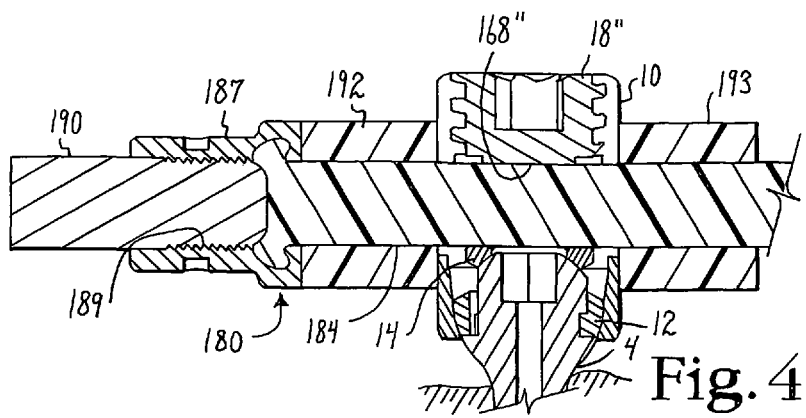
FIG. 44 is an enlarged and partial cross-sectional view taken along the line 44-44 of FIG. 42.

With reference to FIGS. 42-46, the assembly 1 of the invention is shown with alternative closure tops 18" and 18''' as well as with a cord/cord coupler combination 180 and a cord 184. With particular reference to FIGS. 42-44, the assembly 1" is identical to the assembly 1 previously described herein with the exception of the rod 21 is replaced by the cord/cord coupler combination 180 and the closure 18 is replaced by the closure 18". The cord/cord coupler combination 180 further includes a cord 184 with a lip 185 that is fixed within a coupler 187 that further includes inner threads 189 for attaching to a hard rod 190. The illustrated assembly further includes spacers 192 and 193 that may be compressible or not. In operation, the cord 184 is placed in tension. The closure top 18" includes a planar bottom surface 168" sized and shaped to abut against the insert 14 top surface 140 as illustrated in FIG. 41 with respect to the assembly 1', providing independent locking of the shank 4 with respect to the receiver 10. Alternatively, sufficient locking of the bone screw 1" may be provided by the insert 14 outer arm portions pressing against the cylindrical surface 86 of the receiver 10 as illustrated in FIG. 34*b* with respect to the assembly 1. The bottom surface 168" of the closure 18" allows for the cord 180 to slide with respect to the receiver 10, the cord being fixed to the rod 190 at the coupler 187. In such an arrangement, the cord 180 is also fixed to another bone screw 1 (not shown) or fixed to a fixing or blocking structure (not shown) engaging the cord 184 at a location opposite the spacer 193 or other cooperating bone screws.

Figure 45:
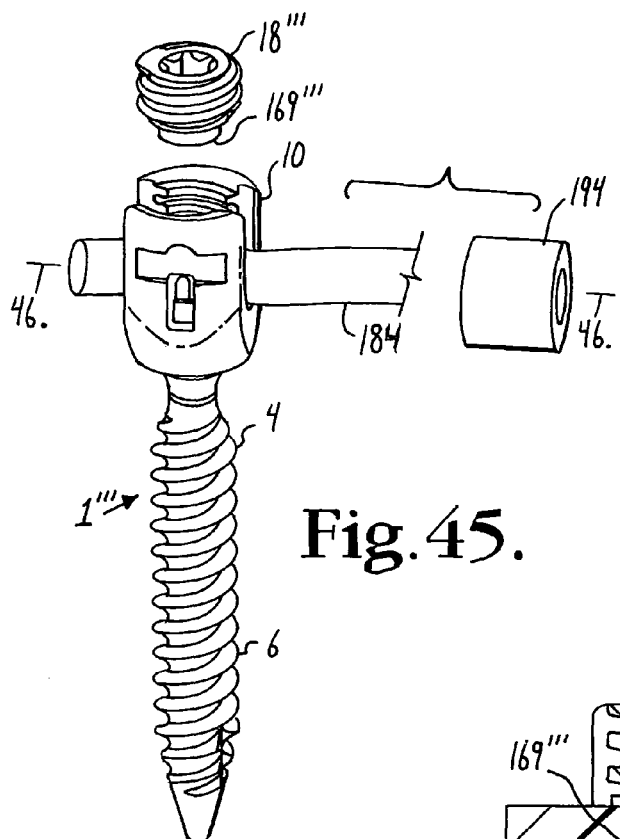
FIG. 45 is a reduced and partial, partially exploded view, showing the assembled receiver, shank, retainer and insert of FIGS. 32-34 with a cord, a spacer and a closure top configured for fixed engagement with the cord.
Figure 46:
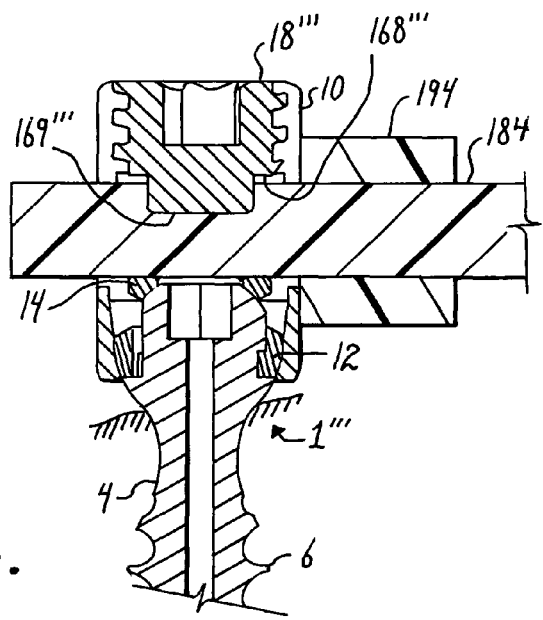
FIG. 46 is an enlarged and partial cross-sectional view, taken along the line 46-46 of FIG. 45 and showing the spacer and closure top in an assembled position.

With reference to FIGS. 45 and 46, the assembly 1''' is identical to the assembly 1 with the exception that the rod 21 is replaced by the cord 184 and the closure 18 is replaced by the closure 18'''. The closure 18''' includes a planar bottom rim 168''' as well as an extension or protrusion 169''' that engages and penetrates the cord 184, holding the cord 184 in fixed engagement with the bone screw assembly 1'''. Also illustrated is a spacer 194 that may be compressible or not. The cord 184 is preferably in tension. For example, the assembly 1''' may be used in combination with the assembly 1" shown in FIGS. 42-44 with the spacer 193 located between the bone screw assemblies 1" and 1''', the cord 180 replacing the cord 184. Thus, the cord 180 would be held in tension between the coupler 187 and the bone screw closure 169'''.

With reference to FIGS. 47-63, an alternative embodiment of a bone anchor assembly according to the invention, generally 201 is illustrated. The assembly 201 includes a shank 204 having a shank body 206 and an upper portion 208, a receiver 210, a cam retainer 212 and a compression or pressure insert 214. The assembly 201 is substantially similar to the assembly 1 with the exception of certain features of the receiver 210 and the insert 214 as will be described in detail below. Unlike the receiver 14, the receiver 214 includes a top surface, rather than an outer or side surface that frictionally engages the receiver 210 to place the insert 214 into frictional engagement with the shank upper portion 208 prior to placement of a rod 21 or other longitudinal connecting member into the receiver 210. Somewhat similar to the insert 14, the insert 214 includes an outer surface that engages a cylindrical surface of the receiver 210 to place the insert 214 into locking engagement with the shank upper portion 208 prior to ultimate locking with a closure top (not shown) that may be the closure top 18, 18', 18" or 18''' previously described herein with respect to the assemblies 1, 1', 1" and 1''', the closure top chosen based upon the type of rod, cord or other longitudinal connecting member being placed within the receiver 210. Similar to the insert 14, the insert 214 may be compressed or squeezed to release locking engagement with the receiver 210 and the shank upper portion 208. The insert 214 advantageously provides such a release-able locking engagement without the key hole slot feature of the insert 14 as will be described in greater detail below.

Figure 47:
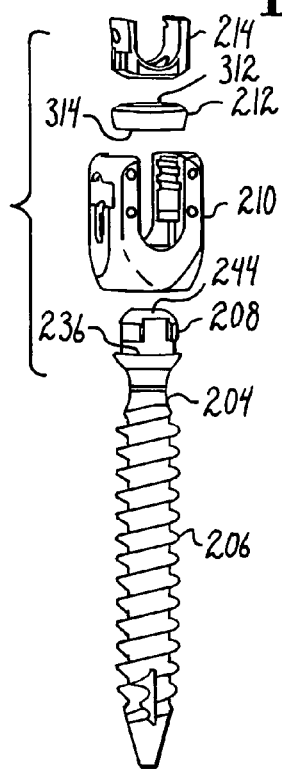
FIG. 47 is an exploded perspective view of an alternative embodiment of a polyaxial bone screw assembly according to the present invention including a shank, a receiver, a retainer and a compression insert.
Figure 48:
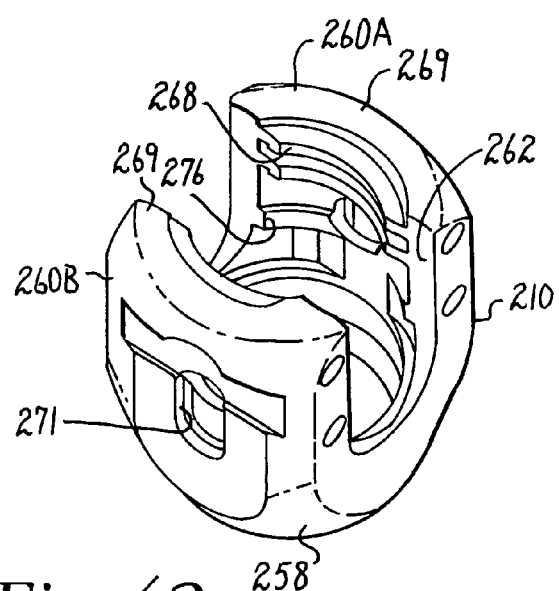
FIG. 48 is an enlarged perspective view of the receiver of FIG. 47.
Figure 49:
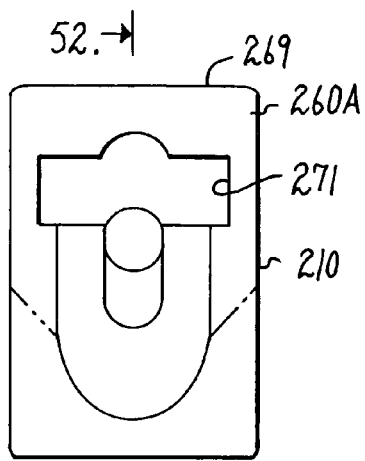
FIG. 49 is an enlarged side elevational view of the receiver of FIG. 47.
Figure 50:
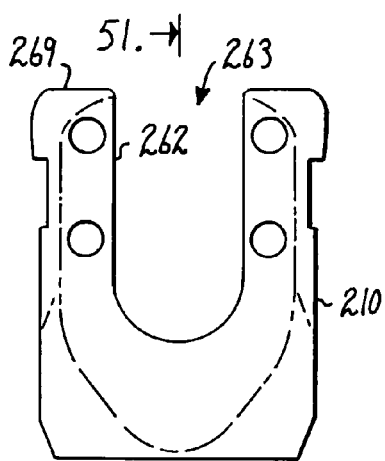
FIG. 50 is an enlarged front elevational view of the receiver of FIG. 47.
Figure 62:
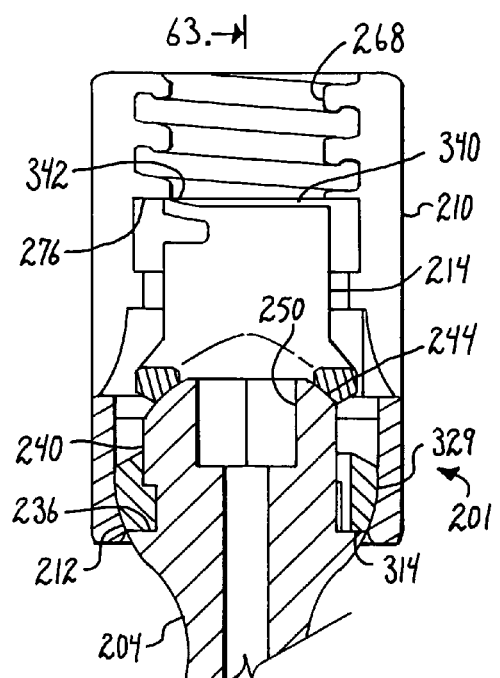
FIG. 62 is a reduced and partial cross-sectional view taken along the line 62-62 of FIG. 61.
Figure 63:
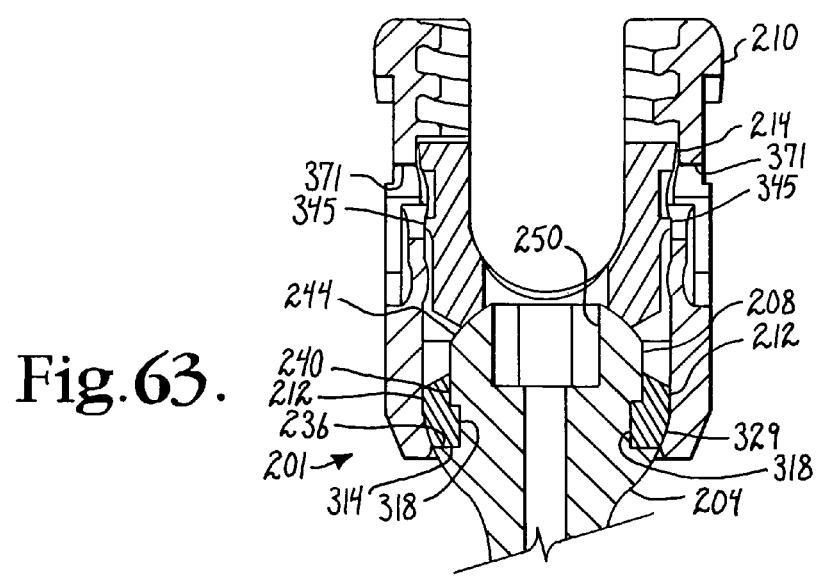
FIG. 63 is a partial cross-sectional view taken along the line 63-63 of FIG. 62.

With particular reference to FIGS. 47, 62 and 63, the shank 204 is identical or substantially similar to the shank 4 of the assembly 1 and therefore, among other things, includes a spherical surface 234, a retainer seat 236, three cam lugs or projections 240, a domed top 244, and an internal drive feature 250, the same or similar to the respective spherical surface 34, retainer seat 36, cam lugs 40, domed top 44 and internal drive 50 previously discussed herein with respect to the shank 4. Similarly, the retainer 212 includes, among other things, a top 312, bottom 314, cam shelves 318 and outer spherical surface 329 that are the same or substantially similar to the respective top 112, bottom 114, cam shelves 118 and outer spherical surface 129 of the retainer 12 previously described herein with respect to the assembly 1. The shank 204 and the retainer 212 are assembled within the receiver 210 in a manner the same or substantially similar to that described previously herein with respect to the shank 4, retainer 12 and receiver 10 of the assembly 1.

Although substantially similar to the receiver 10, the receiver 210 includes some features that are different than the receiver 10 and thus shall be described more fully herein. The receiver 210 includes a base 258, arms 260A and 260B, a U-shaped channel 262, a channel upper opening 263, channel lower seat 264, a guide and advancement structure 268, and arm top surfaces 269, that are the same or substantially similar to the respective base 58, arms 60A and 60B, U-shaped channel 62, channel upper opening 63, channel lower seat 64, guide and advancement structure 68, and arm top surfaces 69 previously described herein with respect to the receiver 10. The receiver 210 further includes a T-shaped tool engagement feature 271 somewhat similar to the feature 71 of the receiver 10. However, The feature 271 further includes a thin crimp wall 275 that provides alignment for the insert 214 similar to the tabs 75 of the receiver 10. The crimp wall 275 is simply pressed inwardly radially toward the insert 214 to prohibit counter-clockwise rotation of the insert 214 with respect to the receiver 210. Similar to the receiver 10, the receiver 210 includes a bottom abutment surface 276 of the guide and advancement run-out located on the arm 260A, the surface 276 frictionally engaging a top surface of the insert 214 as will be described more fully below. Located beneath the surface 276 is a discontinuous cylindrical surface 278 that communicates with another discontinuous cylindrical surface 280 having a diameter smaller than a diameter of the surface 278, the surface 280 cooperating with the insert 214 to lock the insert against the shank upper portion 208 as will be described more fully below. A receive cavity, generally 290 includes an upper cylindrical or slightly conical surface 294 and a spherical seating surface 296 for sliding and ultimate frictional mating with the retainer spherical surface 329. The receiver 210 further includes a lower neck 297 forming an opening 298 at a bottom surface 292 of the receiver 210. Formed in the arm cylindrical surface 280 is a pocket or stop 300 for receiving a projection 304 of the insert 214 to prohibit clockwise movement of the insert 214 with respect to the receiver 210 and thus provide alignment between the insert 214 and the receiver 210 similar to what was previously described herein with respect to the insert 14 and the receiver 10.

Figure 64:
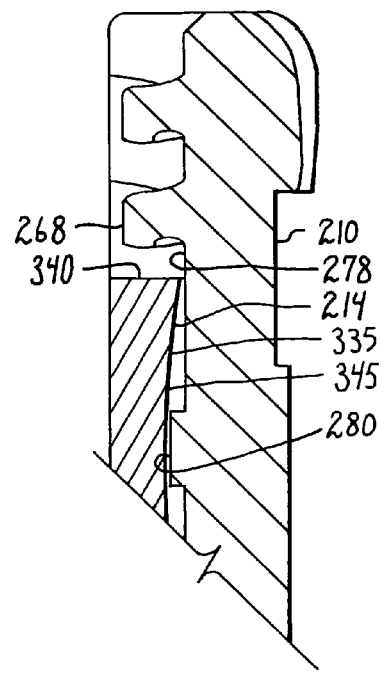
FIG. 64 is an enlarged and partial front elevational view of the assembly of FIG. 61, with portions broken away to show the detail of an initial surface engagement between the insert and receiver.

The insert 214 includes a bore, 330, an inner cylindrical surface 331, an inner spherical surface 332, a substantially cylindrical body 334, upstanding arms 335, a u-shaped channel 336, a channel seat 338 and arm top surfaces 340 substantially similar to the respective bore, 130, inner cylindrical surface 131, inner spherical surface 132, substantially cylindrical body 134, upstanding arms 135, u-shaped channel 136, channel seat 138 and arm top surfaces 140 previously described herein with respect to the insert 14. However, the insert 214 does not include the key-hole slot feature of the insert 214. Instead, at least one or both of the top surfaces 240 includes an upwardly sloping surface feature 342 spaced from a notch 343 formed in the insert arm 335. Thus, the notch 343 may be pressed downwardly toward the body 334. FIG. 55 illustrates an embodiment wherein both surfaces 240 include the surface feature 342, the second feature shown in phantom as 342'. As best illustrated in FIG. 62, the surface 342 engages the receiver surface 276 to hold the insert 214 against the shank upper surface 244 after assembly therewith, so that a friction-fit, non-floppy engagement between the insert 214 and the shank top 208 allows for placement of the angle of the shank 204 with respect to the receiver 210 during surgery and prior to the rod or other connecting member being placed in the receiver 210. Furthermore, the arms 335 include upper portions 345 that flare outwardly and are sized and shaped to cooperate with the surface 280 of the receiver 210 (see FIG. 64) for tight frictional, locking fit between the insert 214 and the shank upper portion 208 when the insert 214 is pushed downwardly toward the receiver base, either by a rod or by a tool. Such locking may be released by a inserting a tool (not shown) in the tool engagement feature 371 and pressing the insert 214 radially inwardly.

The insert 214 is loaded into the receiver 210 in a manner similar to that described above with respect to the insert 14 and the receiver 10 of the assembly 1. The assembly 201 is thereafter fitted with a rod 21 or other longitudinal connecting member and a closure top 18 or cooperating top as described above with respect to the assembly 1.

Figure 65:
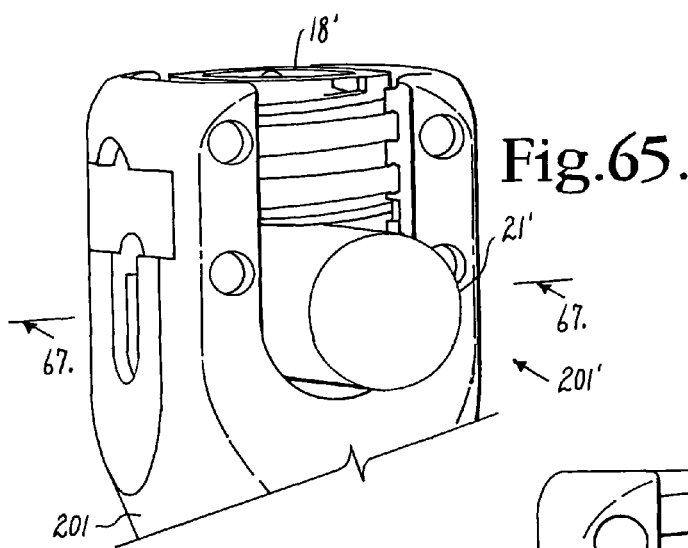
FIG. 65 is an enlarged and partial perspective view of the assembly of FIG. 47 shown assembled with a deformable rod and a closure top.
Figure 66:
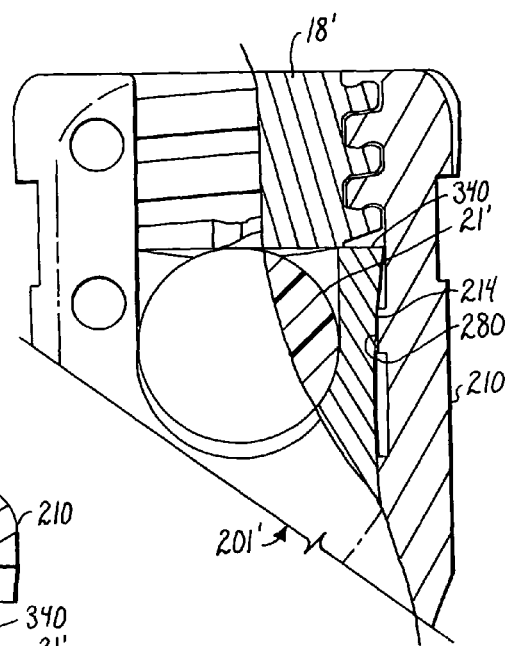
FIG. 66 is an enlarged and partial front elevational view of the assembly of FIG. 65 with portions broken away to show the detail thereof.
Figure 67:
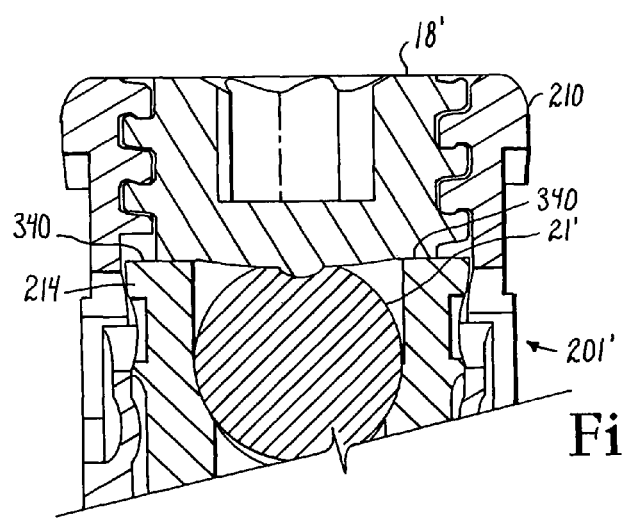
FIG. 67 is an enlarged and partial cross-sectional view taken along the line 67-67 of FIG. 65.

With reference to FIGS. 65-67, the assembly 201 is shown with the deformable rod 21' and the closure top 18' previously described herein. Thus, the resulting assembly is identified as 210'. As illustrated, the closure 18' presses and locks down upon the insert 214 at the surface 340, independently locking the assembly 201 when the assembly is used to capture the deformable rod 21'. Further independent locking is provided by the insert 214 pressing against the receiver surface 280.

It is to be understood that while certain forms of the present invention have been illustrated and described herein, it is not to be limited to the specific forms or arrangement of parts described and shown.

What is claimed and desired to be secured by Letters Patent is as follows:

1. A medical implant comprising:
   a) a receiver having a lower portion with a cavity and a lower opening communicating with the cavity and an upper portion with an upper opening communicating with a longitudinal connecting member receiving channel, the channel communicating with the cavity;
   b) a bone screw shank having a head and a body for fixation to bone, the head having an engagement surface;
   c) a retaining member for capturing the shank head within the receiver, the retaining member having an interior surface sized and shaped for a locking press-fit with respect to the shank, thus fixing engagement with the shank head engagement surface; and
   d) a compression insert positioned in the receiver and operatively locking the shank head with respect to the receiver.

2. The implant of claim 1 wherein the shank and retaining member cooperate in such a manner that a partial rotation between the retaining member and the shank brings the shank and retaining member into the locking press-fit engagement.

3. The implant of claim 2 wherein the shank has a central axis and the partial rotation between the shank and retaining member is about the central axis.

4. The implant of claim 1, wherein the shank head engagement surface is located on an outwardly extending projection, the projection frictionally mating with the retaining member interior surface.

5. The implant of claim 4, wherein the projection is a plurality of projections.

6. The implant of claim 5 wherein the shank head has three outwardly extending projections.

7. The implant of claim 1 wherein the shank head has a lower spherical surface having a radius and the retaining member has an outer spherical surface, a radius of the outer spherical surface being the same as the radius of the shank head lower spherical surface, the outer spherical surface and the retaining member lower spherical surface being adjacent.

8. The implant of claim 7 wherein the shank head lower spherical surface terminates at a shelf, the retaining member being seated on the shelf.

9. The implant of claim 8, wherein the shelf is a first shelf and the shank has a projection with a first inclined surface and the retaining member has a second shelf with a second inclined surface, the first and second inclined surfaces being in frictional engagement with a portion of the retaining member being located between the first shelf and the first inclined surface.

10. The implant of claim 1 wherein the compression insert has first and second positions with respect to the receiver, and wherein in the first position, the insert engages the upper portion of the receiver, the shank head being in movable frictional engagement with the insert, and in the second position, the insert frictionally engaging a lower inner surface of the receiver with the insert being in locked engagement with the shank head.

11. The implant of claim 10 wherein the shank head has a top surface and the insert exclusively engages the top surface and remains spaced from the retaining member in all articulations of the shank with respect to the receiver.

12. The implant of claim 1, wherein the receiver channel is a first channel and the insert further comprises:
   a) a pair of opposed arms forming a second channel, the arms being substantially non-resilient, the second channel in alignment with the first channel; and
   b) an outer resilient structure located near and slightly spaced from a respective arm, the resilient structure being compressible toward the respective arm, the structure, when compressed, resiliently pressing against the receiver during manipulation of the shank with respect to the receiver with the shank head being in frictional, but movable engagement with the insert.

13. The implant of claim 12 wherein the resilient structure is locked against the receiver when the resilient structure is in a neutral to near neutral substantially non-compressed state and the insert is operatively frictionally locked against the shank.

14. The implant of claim 12, wherein the compressible resilient structure and the respective arm form a slit.

15. The implant of claim 12, wherein the outer compressible resilient structure and the respective arm form a through slit running from a top surface to a lower surface of the insert.

16. The implant of claim 12, wherein the outer compressible resilient structure is located at a top surface of the insert.

17. The implant of claim 12, having first and second compressible resilient structures, one structure located at each arm.

18. The implant of claim 1, wherein the receiver includes two inner cylindrical walls of different diameters.

19. A polyaxial bone screw assembly comprising:
a) a shank having a body for fixation to a bone and an upper portion with a top surface, the upper portion having an engagement structure, the upper portion further having a lower partial spherical surface having a first radius;
b) a receiver defining an open channel and having a base with a seating surface partially defining a cavity, the open channel communicating with the cavity, the cavity communicating with an exterior of the base through an opening sized and shaped to receive the shank upper portion therethrough;
c) a retainer for capturing the shank within the receiver, the retainer being sized and shaped for press fit locking engagement with the shank engagement structure, the retainer having an external partial spherical surface having a second radius, the retainer partial spherical surface and the shank lower partial spherical surface sized and shaped for initial pivoting such that the first radius is substantially the same as the second radius; and
d) a compression insert positioned in the receiver, the insert operatively locking the shank head with respect to the receiver seating surface.

20. The assembly of claim 19 wherein the retainer has an interior structure configured to engage and fix against the shank engagement structure, the shank and retainer cooperating in such a manner that a partial rotation between the retainer and the shank brings the shank and retainer structures into locking engagement.

21. The assembly of claim 20 wherein the shank has a central axis and the partial rotation between the shank and retaining member is about the central axis.

22. The assembly of claim 19 wherein the retainer is a continuous closed ring.

23. The assembly of claim 19, wherein the shank upper portion includes a lug for cammed engagement with the retainer.

24. A bone anchor comprising:
a) a receiver having a lower portion with an inner seating surface partially defining a cavity and a lower opening communicating with the cavity and an upper portion with an upper opening communicating with a longitudinal connecting member receiving channel, the channel communicating with the cavity;
b) a bone attachment structure having a head with a top surface, a first planar surface and a first partial spherical surface, the bone attachment structure also having a body for fixation to bone;
c) a retaining member having a second planar surface sized and shaped for press fit engagement with the first planar surface, such that when the first and second planar surfaces are engaged the retaining member is in fixed engagement with the bone attachment structure, the retaining member having a second partial spherical surface, the first and second spherical surfaces having substantially the same radius, both the first and second spherical surfaces receivable by the inner seating surface of the receiver; and
d) a compression insert positioned in the receiver and operatively locking the shank head with respect to the receiver.

25. The bone anchor of claim 24 wherein the bone attachment structure and the retaining member cooperate in such a manner that a partial rotation between the retaining member and the bone attachment structure results in a press fit engagement therebetween.

26. The bone anchor of claim 25 wherein the bone attachment structure has a central axis and the partial rotation between the bone attachment structure and the retaining member is about the central axis.

27. The bone anchor of claim 24, wherein the receiver further comprises a spring tab resiliently pressing against the compression insert at an outer surface thereof, prohibiting rotation of the insert with respect to the receiver.

28. The bone anchor of claim 24 wherein the compression insert has a resilient outer surface sized and shaped to press against the receiver and temporarily hold the insert in frictional engagement with the head top surface for non-floppy positioning of the bone attachment structure with respect to the receiver.

29. The bone anchor of claim 24 wherein the compression insert has a resilient outer surface feature operatively frictionally locking against an inner surface of the receiver partially defining the cavity.

30. The bone anchor of claim 29 wherein the receiver inner surface is a cylindrical surface.

31. The retaining member of claim 24 being an integral one-piece member.

32. A bone anchor assembly comprising:
a) a receiver having a lower portion with a cavity and a lower opening communicating with the cavity and an upper portion with an upper opening communicating with a longitudinal connecting member receiving channel, the channel communicating with the cavity, a first receiver receiver downward facing seating surface partially defining the channel and a second facing surface defining the cavity;
b) a bone screw shank having a head and a body for fixation to bone, the head having an engagement surface for polyaxial motion within the receiver cavity;
c) a retaining member for capturing the shank head within the receiver; and
d) a compression insert positioned in the receiver, the compression insert having an integral resilient structure with a portion thereof partially spaced from the insert, the resilient structure being downwardly compressible toward the insert by the receiver first surface with the insert also pressing downwardly against the shank head during non-floppy articulation of the shank head with respect to the receiver and prior to locking of the assembly.

33. The bone anchor assembly of claim 32, wherein the retaining member further comprises an interior surface sized and shaped for a locking press-fit, fixed engagement with the shank head engagement surface.

34. The bone anchor assembly of claim 32, wherein the insert is loaded into receiver from the top of the receiver.

35. The bone anchor assembly of claim 32, wherein the insert is loaded into receiver from the bottom of the receiver.

36. A bone anchor assembly comprising:
a) a receiver having a lower portion with a cavity and a lower opening communicating with the cavity and an upper portion with an upper opening communicating with a longitudinal connecting member receiving channel, the channel communicating with the cavity, a first receiver downward facing surface and a second receiver surface, the first and second receiver surfaces defining the cavity;
b) a bone screw shank having a head and a body for fixation to bone, the head having an engagement surface for polyaxial motion within the receiver cavity;
c) a compression insert positioned in the receiver, the compression insert having at least one integral resilient structure with a portion thereof partially spaced from the insert, the resilient structure being downwardly compressible toward the insert by the receiver first surface with the insert also pressing downwardly against the shank head during non-floppy articulation of the shank head with respect to the receiver and prior to locking of the assembly.

37. The bone anchor assembly of claim 36, further comprising a retaining member for capturing the shank head within the receiver.

38. A bone anchor assembly comprising:
a) a receiver having a lower portion with a cavity and a lower opening communicating with the cavity and an upper portion with an upper opening communicating with a longitudinal connecting member receiving channel, the channel communicating with the cavity and a receiver downward facing surface for engaging a resilient portion of a compression insert;
b) a bone screw shank having a head and a body for fixation to bone, the head having polyaxial motion within the receiver cavity;
c) a retaining member for capturing the shank head within the receiver; and
d) the compression insert being positioned in the receiver, wherein the compression insert resilient portion is partially spaced from the insert, the resilient portion being downwardly compressible toward the insert when pressed against the receiver downward facing surface and wherein the insert also presses downwardly against the shank head so as to provide non-floppy articulation of the shank head with respect to the receiver prior to locking of the assembly.

* * * * *